US012629380B2

(12) United States Patent
Westrin et al.

(10) Patent No.: US 12,629,380 B2
(45) Date of Patent: May 19, 2026

(54) ORAL FILM UNIT DOSAGE FORM

(71) Applicant: SWIPP AB, Lund (SE)

(72) Inventors: Bengt Westrin, Lund (SE); Nicolas Rollet, Chevigny-Saint-Sauveur (FR); Justine de la Prunarède, Nuits-Saint-Georges (FR)

(73) Assignee: Swipp AB, Lund (SE)

( * ) Notice: Subject to any disclaimer, the term of this patent is extended or adjusted under 35 U.S.C. 154(b) by 271 days.

(21) Appl. No.: 18/685,079

(22) PCT Filed: Aug. 25, 2022

(86) PCT No.: PCT/EP2022/073686

§ 371 (c)(1),
(2) Date: Feb. 20, 2024

(87) PCT Pub. No.: WO2023/025890

PCT Pub. Date: Mar. 2, 2023

(65) Prior Publication Data

US 2024/0374611 A1    Nov. 14, 2024

(30) Foreign Application Priority Data

Aug. 25, 2021    (EP) .................................... 21193042

(51) Int. Cl.
| | |
|---|---|
| *A61K 9/00* | (2006.01) |
| *A61K 9/70* | (2006.01) |
| *A61K 31/5513* | (2006.01) |
| *A61K 31/5517* | (2006.01) |
| *A61K 47/10* | (2017.01) |
| *A61K 47/14* | (2017.01) |
| *A61K 47/26* | (2006.01) |
| *A61K 47/38* | (2006.01) |
| *A61P 25/18* | (2006.01) |
| *A61P 25/22* | (2006.01) |
| *A61P 25/24* | (2006.01) |

(52) U.S. Cl.
CPC ........ *A61K 31/5517* (2013.01); *A61K 9/0053* (2013.01); *A61K 9/7007* (2013.01); *A61K 47/10* (2013.01); *A61K 47/14* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 7,585,493 B2 | 9/2009 | Hale et al. | |
| 10,744,086 B2 | 8/2020 | Lim et al. | |
| 11,173,114 B1 | 11/2021 | Fuisz et al. | |
| 2010/0181387 A1 | 7/2010 | Zaffaroni et al. | |

| | | | |
|---|---|---|---|
| 2017/0119660 A1 | 5/2017 | Temtsin-Krayz et al. | |
| 2017/0304319 A1* | 10/2017 | Westrin ..................... | A61P 7/10 |
| 2023/0130055 A1 | 4/2023 | Wargacki et al. | |

FOREIGN PATENT DOCUMENTS

| | | | |
|---|---|---|---|
| CN | 1830447 A1 | 9/2006 | |
| CN | 111320632 A | 6/2020 | |
| CN | 116041351 A | 5/2023 | |
| EP | 2233134 A1 | 9/2010 | |
| MX | 2010005067 A | 11/2011 | |
| TW | 1238067 B | 8/2005 | |
| WO | 1993018752 A1 | 9/1993 | |
| WO | 1994027608 A1 | 12/1994 | |
| WO | 1998017251 A1 | 4/1998 | |
| WO | 1999055312 A2 | 11/1999 | |
| WO | 2000050007 A1 | 8/2000 | |
| WO | 2000062764 A1 | 10/2000 | |
| WO | 2001030288 A1 | 5/2001 | |
| WO | 2002011768 A1 | 2/2002 | |
| WO | 2002089849 A1 | 11/2002 | |
| WO | 2003030881 A1 | 4/2003 | |
| WO | 2003084517 A2 | 10/2003 | |
| WO | 2005016321 A1 | 2/2005 | |
| WO | 2005039543 A1 | 5/2005 | |
| WO | 2005048996 A2 | 6/2005 | |
| WO | 2005081825 A2 | 9/2005 | |
| WO | 2006041942 A2 | 4/2006 | |
| WO | 2007034287 A2 | 3/2007 | |
| WO | 2007112581 A1 | 10/2007 | |
| WO | 2008018561 A1 | 2/2008 | |
| WO | 2008038003 A2 | 4/2008 | |
| WO | 2008040534 A2 | 4/2008 | |

(Continued)

OTHER PUBLICATIONS

Jithendra, et al., "Formulation Development and In-Vitro Evaluation of Midazolam Solid Dispersions and Their Buccal Flash Disintegrating Films", Panacea Journal of Pharmacy and Pharmaceutical Sciences, 2015:4(4), pp. 801-816.
Kathpalia, et al., "An Introduction to Fast Dissolving Oral Thin Film Drug Delivery Systems: A Review", Current Drug Delivery, 2013, 10, pp. 667-684.
Reddy, Muthadi Radhika, "An Introduction to Fast Dissolving Oral Thin Film Drug Delivery Systems: A Review", Journal of Pharmaceutical Sciences and Research, vol. 12(7), 2020, pp. 925-940.
Rogawski, et al., "Diazepam buccal film for the treatment of acute seizures", Epilepsy & Behavior 101, 2019 , pp. 1-4.

(Continued)

*Primary Examiner* — Brian Gulledge
(74) *Attorney, Agent, or Firm* — Weston R. Gould; Dinsmore & Shohl LLP

(57) ABSTRACT

The present invention relates to oral films containing an active pharmaceutical ingredient (API) capable of providing seizure relief and one or more film-forming polymers, the use of such films, for example for the acute treatment of ongoing seizures, and methods for preparing such films. The film according to the invention is characterized by a rapid dissolution in the buccal cavity followed by a rapid and high systemic absorption.

20 Claims, 3 Drawing Sheets

(56) References Cited

FOREIGN PATENT DOCUMENTS

| WO | 2008073779 A2 | 6/2008 |
| WO | 2009076764 A1 | 6/2009 |
| WO | 2009089494 A2 | 7/2009 |
| WO | 2009111648 A1 | 9/2009 |
| WO | 2009113703 A2 | 9/2009 |
| WO | 2010009335 A2 | 1/2010 |
| WO | 2010044736 A1 | 4/2010 |
| WO | 2010069050 A1 | 6/2010 |
| WO | 2010151020 A2 | 12/2010 |
| WO | 2011053251 A1 | 5/2011 |
| WO | 2011152926 A1 | 12/2011 |
| WO | 2013121663 A1 | 8/2013 |
| WO | 2013172999 A1 | 11/2013 |
| WO | 2015015303 A2 | 2/2015 |
| WO | 2015065547 A1 | 5/2015 |
| WO | 2016111725 A1 | 7/2016 |
| WO | 2016134454 A1 | 9/2016 |
| WO | 2017009446 A1 | 1/2017 |
| WO | 2018156214 A1 | 8/2018 |
| WO | 2021097247 A1 | 5/2021 |
| WO | WO2022/151732 A1 | 7/2022 |
| WO | WO2022/192476 A1 | 9/2022 |
| WO | WO2023/025890 A1 | 3/2023 |

OTHER PUBLICATIONS

Soroushnai, et al., "Development and Evaluation of an Anti-Epileptic Oral Fast-Dissolving Film with Enhanced Dissolution and In vivo Permeation", Bentham Science, 2018, 15, 1924-1304.

Tomlin, Steve, "Medicines tailored for children—the introduction of buccal midazolam", The Pharmaceutical Journal, 2011, vol. 287, pp. 161-162.

European Medicines Agency Science Medicines Health, "Buccolam", 2011.

Wasilewska, et al., "How to assess orodispersible film quality? A review of applied methods and their modifications", Acta Pharm. 69 (2019), pp. 155-176, DOI: 10.2478/acph-2019-0018.

International Search Report and Written Opinion of Corresponding International Application No. PCT/EP2022/073686, mailed Dec. 14, 2022, 16 pages.

Belle, et al., The effects of an oral contraceptive containing ethinyloestradiol and norgestrel on CYP3A activity, J Clin Pharmacol, 53: 67-74, 2002.

* cited by examiner

E

F

ORAL FILM UNIT DOSAGE FORM

CROSS REFERENCE TO RELATED APPLICATIONS

This application is a U.S. National Stage under 35 U.S.C. § 371 of international application number PCT/EP2022/073686 filed Aug. 25, 2022, and which depends from and claims priority to European application number 21193042.5 filed Aug. 25, 2021, the entire contents of which are incorporated herein by reference.

TECHNICAL FIELD

The present invention relates to oral films containing an active pharmaceutical ingredient (API) capable of providing seizure relief and one or more film-forming polymers, the use of such films, for example for the acute treatment of ongoing seizures, and methods for preparing such films.

BACKGROUND

Midazolam is a benzodiazepine drug substance. It is available as injection products for a variety of indications, but also as buccal solutions (typically up to 10 mg midazolam, per pre-determined dose) for the acute treatment of ongoing seizures, and as oral solutions or syrups (typically 2 mg/mL, with recommended dose of up to 20 mg) for moderate sedation in paediatric patients prior to diagnostic or therapeutic procedures or moderate sedation/pre-sedation before induction of anaesthesia. For those two uses of midazolam, i.e. seizure treatment and pre-sedation, it is clearly advantageous to have products that are easy-to-use and that may improve compliance.

Midazolam is commercially available as medicinal product containing midazolam hydrochloride, for example in the form of oral syrups sold for example under the trade name VERSED®, which contains 2 mg/mL of midazolam (specified as the base), and in the form of BUCCOLAM® oromucosal solution which contains 5 mg/mL midazolam (specified as the base) in pre-filled syringes of 0.5 mL, 1 mL, 1.5 mL or 2 mL, i.e. pre-determined doses of 2.5 mg, 5 mg, 7.5 mg and 10 mg, respectively. Midazolam has also been marketed in the form of its maleate salt, for example in tablets containing 7.5 or 15 mg per tablet under the trademark DORMICUM®, and in EPISTATUS® oromucosal solution which contains 10 mg/mL midazolam (specified as the base). BUCCOLAM® and EPISTATUS® oromucosal solutions are examples of midazolam products that are formulated for buccal administration.

The use of oral film as dosage form has been proposed for a large number of drug substances, for example amlodipine, buprenorphine, dexamethasone, donepezil, loperamide, naloxone, nicotine, odansetron and many others. Some examples of approved drug products for which there are human pharmacokinetic or clinical data are SUBOXONE® sublingual film (buprenorphine and naloxone) used for the treatment of addiction to opioid products; BELBUCA® buccal film (buprenorphine) used for the treatment of severe pain; and SETOFILM® orodispersible film (odansetron) used for prophylaxis or treatment of nausea and vomiting. These products also exemplify the three main categories of oral films: sublingual films, buccal films and orodispersible films (ODF), respectively, which differ with regard to the site of administration and the predominant route of absorption into systemic circulation. It is generally considered that for a sublingual film, the predominant route of absorption can be either transmucosal (i.e., in the oral cavity) or oral (i.e., in the gastrointestinal tract), for a buccal film it is predominately transmucosal, and for an orodispersible film it is predominately oral. However, there is usually some oral-gastrointestinal absorption even if the intention is buccal-transmucosal absorption, and vice versa. There are also oral films intended for local effects (non-systemic), as well as a large number of non-prescription products (OTC).

The main advantages with oral films are generally considered to be that they are easy to use, that they do not require water for the administration, that they are especially feasible for certain patient groups (e.g. those with difficulties swallowing tablets, or those that are unconscious when the treatment is given) and in treatment of diseases or conditions where compliance can be an issue. In addition, for buccal or sublingual films for which the predominant absorption route is transmucosal, the so-called first-pass effect is eliminated or reduced. Moreover, the time to achieve effective plasma levels can often be faster for an oral film than for a conventional tablet.

There are also disadvantages and challenges with oral films. One example is the limitation of the strength, i.e. the content of the active pharmaceutical ingredient, due to the minute size of an oral film. Typically, due to that, the strength of an oral film has to be 10 mg or less, although in rare cases it can be higher. This limitation of the strength is especially challenging for films in which the substance is intended to be dissolved inside the film (a state which is sometimes also called "solid solution" or "molecular dispersion"). In such films, and especially at concentrations of 15 wt % and higher, the substance may be prone to precipitate in the form of solid particles inside the film, which may be amorphous or crystal-line of different polymorphs. This may have an impact on the film's appearance and dissolution rate, and even on the human bioavailability and clinical efficacy of the product. Such precipitation is thus very unbeneficial and must be avoided both during manufacturing and storage.

Another challenge is the film manufacturing which is a less established technology than for example tablet manufacturing. The film composition has to be such that the mechanical property of the film allows for a continuous coating process and converting process, the latter of which can be rather high speed and requires strength and plasticity of the polymer-based film. Physical stability is yet another challenge, which is partly associated with the high concentrations needed to achieve the desired strengths. For example, for films of normal size and thickness, a 10 mg strength means drug substance concentrations inside the film of about 30%. For a sparingly soluble drug substance, intended to be dissolved in the film, such a drug concentration can induce precipitation during storage.

Jithendra et al. 2015 describes a film prepared by first preparing a solid dispersion of midazolam and one or more other excipients (e.g. PEG-4000, poloxamer-188, and hydroxypropyl β-cyclodextrin), then "pulverizing" that material and finally using the resulting material as a carrier for the active ingredient for solvent casting preparation of a buccal film with hydroxypropyl methylcellulose (HPMC) as film forming polymer. The rationale for this two-staged approach is to improve the solubility/dissolution rate of the drug substance. The film thicknesses are reported to be between 600-870 μm. The midazolam concentration in the films is not explicitly reported by Jithendra et al. 2015 but it can be deduced that the concentration would vary between approximately 2.3 wt % (if the film has an area of 5 cm² and a thickness of 870 μm) and approximately 8.3 wt % (if 2 cm² and thickness 600 μm) for a film comprising 10 mg midazolam.

Soroushnai et al. 2018 describes another two-staged approach with rationale to incorporate a "high drug dose" despite "midazolam's high lipophilicity and poor water solubility". Midazolam hydrochloride is used, with which a midazolam nanosuspension is first prepared, by a high-pressure homogenization technique, using N-trimethyl chitosan, Tween-80 and polaxamer-188 as excipients. Next, the nanosuspension is freeze-dried, and finally the resulting material is used for solvent casting preparation of a "fast-dissolving oral film" with hydroxypropyl methylcellulose or pullulan as film forming polymer. The reported midazolam concentration in the film is 15 wt %. The optimized and proposed best-performing formulation, which has pullulan as film forming polymer, is reported to be "stable for 3 months" but the occurrence of potential midazolam precipitation was not studied.

WO 2017/009446 describes a "bio-adhesive film or wafer" which is prepared in a more conventional way, i.e. solvent casting preparation without any preceding preparation of any midazolam intermediate material. HPMC is used as a film-forming polymer. The intended films are described as having 0.25-2 mg midazolam strengths or even as low as 0.1 mg, or are described as typically containing 0.5-20 mg midazolam per gram of film, which corresponds to 0.05-2 wt % of midazolam in the film.

Rogawski et al 2019 discloses a buccal film containing diazepam but does not disclose any information about the film design or composition other than that HPMC is used as a film-forming polymer CN1830447A describes a film containing midazolam maleate, and for which the film-forming polymer is either PVA or HPMC, and the plasticizer is either PEG-400 or glycerol. It is described that the dissolution rate is 7 times higher than a tablet and that all components dissolves within 30 seconds.

There is thus a need for the development of a buccal film containing 10 mg midazolam, or a pharmaceutically acceptable salt thereof, or more, yet having an area and thickness that are feasible for buccal films or other oral films which means that the concentration of midazolam inside the film will be very high, e.g. 30 wt % and which means that the formulation design must be such that it prevents said substance from precipitating during storage. Furthermore, the film should have moderately high dissolution rate, to prevent a partial loss of the dose in case the patient is drooling or swallowing saliva after the administration of the film.

SUMMARY

The present inventors have developed a unit dosage form in the form of an oral film with high concentration of midazolam or a pharmaceutically acceptable salt thereof. The unit dosage form of the present invention has been demonstrated to have much higher bioavailability than a buccal solution of the same strength.

In one aspect, the present invention relates to a unit dosage form in the form of an oral film comprising:
   a) at least 20 wt % (defined as the base) midazolam or a pharmaceutically acceptable salt thereof; and
   b) 35 to 70 wt % HPMC, wherein the HPMC is a mixture of:
      i) Hypromellose 2910, 3 mPa·s; and
      ii) Hypromellose 2910, 50 mPa·s.

In one aspect, the present invention relates to a process for producing a unit dosage as defined herein, the process comprising the steps of:
   a) mixing the midazolam or a pharmaceutically acceptable salt thereof and HPMC in a solvent to provide a wet mix solution; and
   b) casting the wet mix obtained in step a) and drying it to provide a final film.

In one aspect, the present invention relates to a unit dosage form as defined herein for use in the acute treatment of seizures in a subject.

DESCRIPTION OF DRAWINGS

FIG. 1a: Visual appearance of A9. FIG. 1b: Microscopy of A9 with about 5-10 times magnification compared with FIG. 1a. FIG. 1c: Visual appearance of A10. FIG. 1d: Microscopy of A10 with about 5-10 times magnification compared with FIG. 1c. FIG. 1e: Visual appearance of A11. FIG. 1f: Microscopy of A11 with about 5-10 times magnification compared with FIG. 1e.

DETAILED DESCRIPTION

Unit Dosage Form

Figure 1:
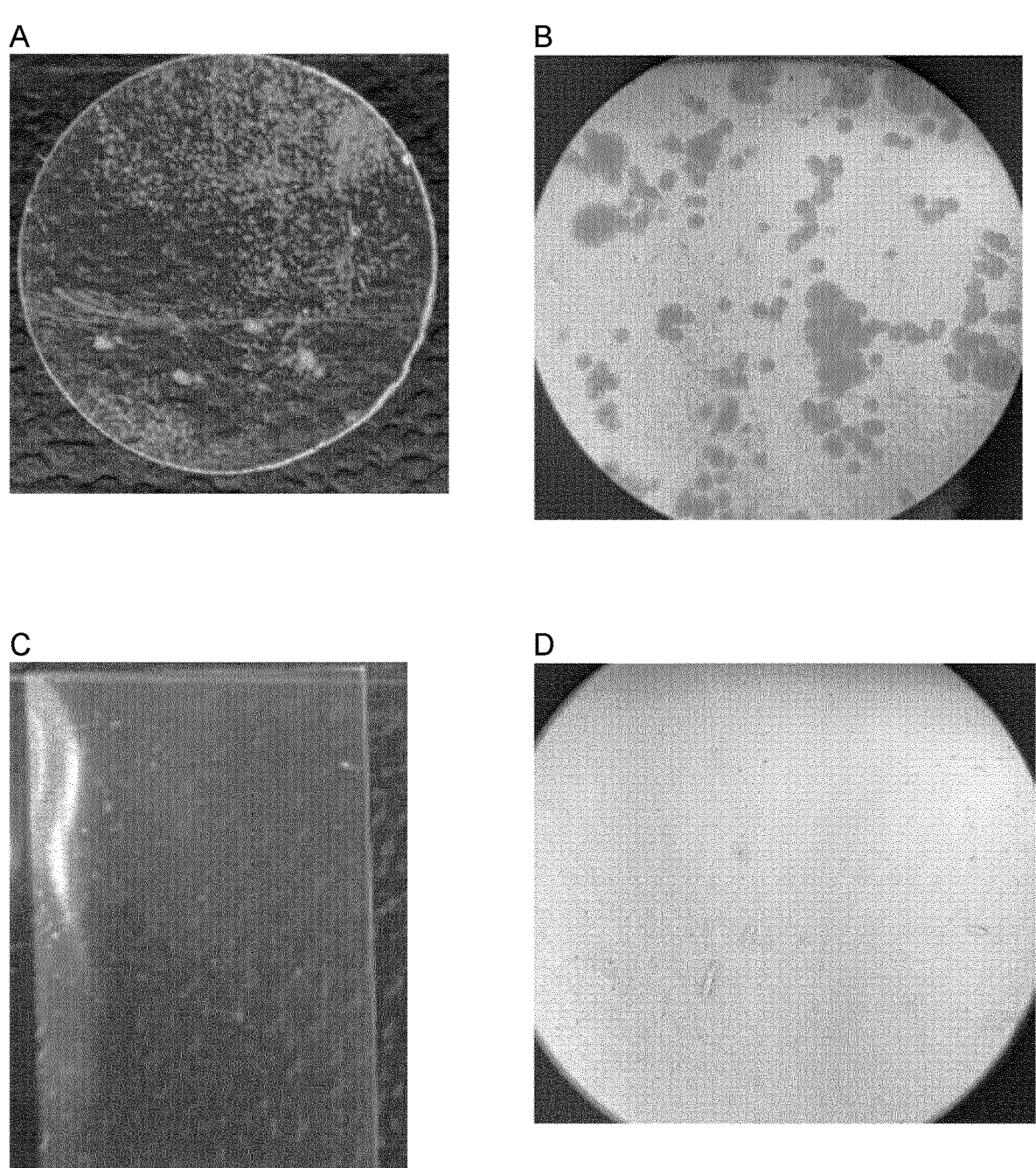
FIG. 1. Appearance of formulations A9 (14% glycerol), A10 (5%) and A11 (0%).
Figure 1:
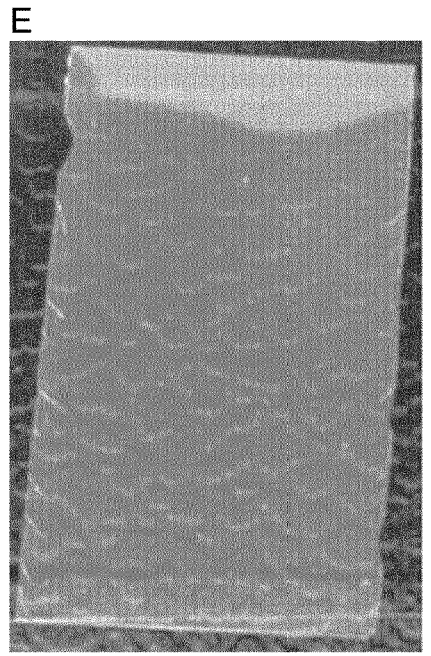
Figure 1:
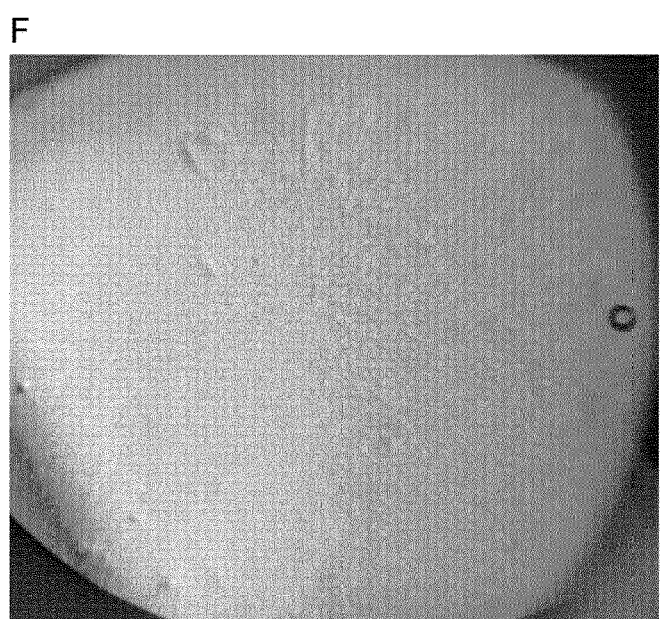

In one aspect, the present invention relates to a unit dosage form in the form of an oral film comprising an active pharmaceutical ingredient (API) and a film-forming polymer. The term "unit dosage form" refers to physically discrete units suitable as unitary dosage for subjects undergoing treatment, with each unit containing a predetermined quantity of active material calculated to produce the desired therapeutic effect. The term "oral film" as used herein refers to sublingual, buccal and orodispersible films (ODF), as well as any other films placed into the oral cavity aiming at local or systemic effects.

In one embodiment, the unit dosage form is for buccal administration. In one embodiment, the film is a mucoadhesive film. The term "buccal administration" as used herein refers to administration to the space in the oral cavity that is outside the teeth when the jaws are closed, such as for example the inside of the cheek or under the upper lips.

Oromucosal solutions are typically applied into the buccal cavity and hence they may also be called buccal solutions, and the absorption route is typically transmucosal which may also be called buccal.

In one embodiment, the film has a relatively high dissolution rate for the rapid delivery of API into systemic circulation.

To avoid slow in vivo the dissolution rate, it may be favourable if the API is dissolved in the film, i.e. not suspended. In addition, the film should not be too thick, but yet thick enough to accommodate the intended dose of the API. Further, the unit dosage form should be stable for storage. Such storage stability does not just comprise chemical stability, but also physical stability, e.g., that the API, if intended to be dissolved in the film, should not precipitate during storage.

In one aspect, the present invention relates to a unit dosage form in the form of an oral film comprising:

a) at least 20 wt % (defined as the base) midazolam or a pharmaceutically acceptable salt thereof; and b) 35 to 70 wt % HPMC, wherein the HPMC is a mixture of:

i) Hypromellose 2910, 3 mPa·s; and ii) Hypromellose 2910, 50 mPa·s.

Dissolution Rate

In a preferred embodiment, the unit dosage form of the present invention has a relatively high dissolution rate. The term "relatively high dissolution rate" as used herein means that at least 85% of the API has been dissolved within 10 minutes but no more than 95% has been dissolved within 5 minutes in the USP Dissolution Apparatus 2—Paddle. Hence, the term "relatively high dissolution rate" does not include instantaneous dissolution, such as the film being completely dissolved in vitro within one minute. It is an aim of the present invention to provide a unit dosage form wherein the administered dose is not instantaneously released and thereby it is not instantaneously mixed with saliva either, since such film, i.e. with an instantaneous dissolution rate, may suffer from the same drawbacks as an oromocusal solution, such as drooling induced or swallowing induced dose losses.

The dissolution rate may be measured using the United States Pharmacopeia (USP) Dissolution Apparatus 2—Paddle (37° C.±0.5° C.) in order to predict in vivo drug release profiles, see Example 10 for further details.

In one embodiment, at least 85% of the API has been dissolved within 10 minutes in the USP Dissolution Apparatus 2—Paddle, such as at least 90%, such as at least 95% of the API has been dissolved within 10 minutes.

In one embodiment, the API is midazolam and at least 85% of the midazolam has been dissolved within 10 minutes in the USP Dissolution Apparatus 2—Paddle (37° C.±0.5° C., 75 rpm in 1000 mL phosphate buffer pH 6.8), such as at least 90%, such as at least 95% of the midazolam has been dissolved within 10 minutes.

In one embodiment, at least 85% of the midazolam, or pharmaceutically acceptable salt thereof, has been dissolved within 10 minutes in the USP Dissolution Apparatus 2—Paddle (37° C. 0.5° C., 75 rpm in 1000 mL phosphate buffer pH 6.8), such as at least 90%, such as at least 95% of the midazolam, or pharmaceutically acceptable salt thereof, has been dissolved within 10 minutes.

In one embodiment, wherein at least 90% of the midazolam has been dissolved within 10 minutes in the USP Dissolution Apparatus 2—Paddle, such as at least 95%, such as at least 98%, such as 100% of the midazolam, or pharmaceutically acceptable salt thereof, has been dissolved within 10 minutes.

In one embodiment, at least 85% of the midazolam, or pharmaceutically acceptable salt thereof, has been dissolved within 5 minutes in the USP Dissolution Apparatus 2—Paddle (37° C.±0.5° C., 75 rpm in 1000 mL phosphate buffer pH 6.8), such as at least 90%, such as at least 95% of the midazolam, or pharmaceutically acceptable salt thereof, has been dissolved within 5 minutes.

In one embodiment, at least 90% of the midazolam has been dissolved within 5 minutes in the USP Dissolution Apparatus 2—Paddle, such as at least 95%, such as at least 98%, such as 100% of the midazolam, or pharmaceutically acceptable salt thereof, has been dissolved within 5 minutes.

In one embodiment, no more than 90% of the midazolam, or pharmaceutically acceptable salt thereof, has been dissolved within 1 minute in the USP Dissolution Apparatus 2—Paddle.

In one embodiment, no more than 85% of the midazolam, or pharmaceutically acceptable salt thereof, has been dissolved within 1 minute in the USP Dissolution Apparatus 2—Paddle, such as no more than 80%, such as no more than 75%, such as no more than 70%, such as no more than 65%, such as no more than 60%, such as no more than 60%, such as no more than 55%, such as no more than 50%, such as no more than 45%, such as no more than 40% of the midazolam, or pharmaceutically acceptable salt thereof, has been dissolved within 1 minute.

In one embodiment, no more than 95% of the midazolam, or pharmaceutically acceptable salt thereof, has been dissolved within 5 minutes in the USP Dissolution Apparatus 2—Paddle.

In one embodiment, no more than 95% of the midazolam, or pharmaceutically acceptable salt thereof, has been dissolved within 5 minutes in the USP Dissolution Apparatus 2—Paddle, such as no more than 90%, such as no more than 85%, such as no more than 80%, such as no more than 75%, such as no more than 70%, such as no more than 65%, such as no more than 60%, such as no more than 60%, such as no more than 55%, such as no more than 50%, such as no more than 45%, such as no more than 40% of the midazolam, or pharmaceutically acceptable salt thereof, has been dissolved within 5 minutes.

In one embodiment, at least 85% of the midazolam, or pharmaceutically acceptable salt thereof, has been dissolved within 10 minutes but no more than 95% has been dissolved within 5 minutes in the USP Dissolution Apparatus 2—Paddle.

In one embodiment, at least 90% of the midazolam, or pharmaceutically acceptable salt thereof, has been dissolved within 10 minutes but no more than 90% has been dissolved within 5 minutes in the USP Dissolution Apparatus 2—Paddle.

The film dissolution rate may also be assessed by the method as described in Example 1, wherein the film is placed in water and shaken, and the time when the film starts to disintegrate/dissolve is noted as well as the time when at least 90% of the film area has been dissolved, according to an assessment with the naked eye. However, in this case it is not the API dissolution that is studied, as is the case with the USP method described above. Instead, it is the disintegration and dissolution of the polymer film matrix that is studied.

Active Pharmaceutical Agent (API)

In one embodiment, the unit dosage form of the present invention comprises an API that is capable of providing relief from ongoing seizures. In one embodiment, the API is an anticonvulsant. In one embodiment, the API has a sedative effect, such as an API being useful in moderate sedation before diagnostic, therapeutic or surgical procedures or pre-sedation before anaesthesia. In one embodiment, the API is selected from the group consisting of benzodiazepines and benzodiazepine-like substances.

The term "benzodiazepine" as used herein refers generically to a class of drugs that act as central nervous system depressants with sedative, hypnotic, anxiolytic, anticonvulsant, muscle relaxant, and amnesic actions through the positive modulation of the GABA-A receptor complex.

The term "benzodiazepine-like substances" (also known as nonbenzodiazepines or Z-drugs) refers to a class of compounds which pharmacodynamics are almost identical to benzodiazepines and therefore exhibit similar benefits, side-effects, and risks. However, benzodiazepine-like substances differ from benzodiazepines on a molecular level.

In one embodiment, the API is selected from the group consisting of midazolam, diazepam, alprazolam, brotizolam, cinolazepam, clizolam, clobazam, clonazepam, clonazolam, clorazepate, cloxazolam, diclazepam, estazolam, flubromezepine, flunitrazepam, flurazepam, flutoprazepam, kvazepam, lorazepam, loprazolam, lormetazolam metizolam, nitrazepam, oxazepam, phenazepam, temazepam, triazolam and pharmaceutically acceptable salts thereof. In one embodiment, the API is midazolam, diazepam, clobazam, clonazepam, lorazepam or a pharmaceutically acceptable salt thereof. In one embodiment, the API is midazolam, diazepam, or a pharmaceutically acceptable salt thereof.

In a preferred embodiment, the API is midazolam (8-chloro-6-(2-fluorophenyl)-1-methyl-4H-imidazo[1,5-a] [1,4]benzodiazepine, CAS number 59467-70-8) or a pharmaceutically acceptable salt thereof. Said pharmaceutically acceptable salt may be selected from hydrochloride or maleate. In one embodiment, the API is midazolam hydrochloride.

When the API is a salt of a base, the amounts given for the API refers to the amount of the free base. For example, "10 mg midazolam" refers to 10 mg of midazolam specified as the free base, even if midazolam was added as a salt during the preparation of the unit dosage form.

In one embodiment, the unit dosage form comprises at least 2.5 mg of API, such as at least 5 mg, such as at least 10 mg of API. In one embodiment, the unit dosage form comprises no more than 20 mg of API, such as no more than 15 mg, such as no more than 10 mg of API. In one embodiment, the unit dosage form comprises 2.5 to 20 mg of API, such as 5 to 15 mg, such about 10 mg, such as about 7.5 mg, such as about 5 mg of API. In one embodiment, the unit dosage form comprises 2.5 to 20 mg (defined as the base) of midazolam or a pharmaceutically acceptable salt thereof, such as 5 to 15 mg, such about 10 mg of midazolam or a pharmaceutically acceptable salt thereof. In one embodiment, the unit dosage form comprises about 10 mg midazolam. In one embodiment, the unit dosage form comprises about 7.5 mg midazolam. In one embodiment, the unit dosage form comprises about 5 mg midazolam.

In one embodiment, the concentration of API in the film is at least 10 wt %, such as at least 15 wt %, such as at least 20 wt %, such as at least 25 wt %, such as at least 30 wt %. In one embodiment, the concentration of API in the film is no more than 80 wt %, such as no more than 70 wt %, such as no more than 60 wt %, such as no more than 50 wt %, such as no more than 40 wt %. In one embodiment, the concentration of API in the film is in the range of 10 to 60 wt %, such as in the range of 15 to 40 wt %, such as in the range of 15 to 25 wt % or such as in the range of 30 to 60 wt %, for example in the range of 20 to 40 wt %, such as in the range of 25 to 35 wt %, such as in the range of 30 to 35 wt %. In one embodiment, the concentration of midazolam or pharmaceutically acceptable salt thereof is 25 to 40 wt %, such as 30 to 35 wt % (defined as the base).

In one embodiment, the API is midazolam and to achieve a strength of 10 mg midazolam of the unit dosage form, while the unit dosage form has a feasible film thickness allowing for a relatively high film dissolution rate (such as 70 to 110 μm thickness) and a convenient size (e.g. 1.5×2.5 cm), the concentration of midazolam in the dry film must be about 25 to 40 wt %.

The term "strength" is used herein to describe the content of the active pharmaceutical ingredient and is typically expressed in milligram (mg) or microgram (μg). As an oral film is a unit dose dosage form, said strength is typically identical to the dose to be administered to the patient, although sometimes more than one unit dosage can be administered and sometimes just a part of one unit dosage is administered. For a film with dimensions of 15×15 mm, and a coat weight of 100 g/m2, a strength of 10 mg means that the concentration of drug substance is about 27 wt % inside the film.

In one preferred embodiment, the midazolam or pharmaceutically acceptable salt thereof is midazolam hydrochloride.

To increase the dissolution rate, it may be favourable if the API is dissolved in the film, i.e. not suspended. In one embodiment, the API is predominately in dissolved state in the film. In one embodiment, at least 60 wt %, such as at least 70 wt %, such as at least 80 wt %, such as at least 90 wt %, such as at least 95 wt %, such as at least 98 wt % of the API is in dissolved state in the film. In one embodiment, the concentration of API in the film is in the range of 15 to 35 wt % and at least 60 wt %, such as at least 70 wt %, such as at least 80 wt %, such as at least 90 wt %, such as at least 95 wt %, such as at least 98 wt % of the API is in dissolved state in the film.

In one embodiment, the unit dosage form comprises two or more active pharmaceutical ingredients. In one embodiment, the total concentration or amount or API in a unit dosage form comprising two or more active pharmaceutical ingredients is equal to any of the levels presented above.

Film-Forming Polymers

The unit dosage form of the present invention comprises one or more film-forming polymers.

In one embodiment, the film-forming polymer is selected from the group consisting of HPMC, alginate, acrylate, PVP, gum, carrageenan, chitosan, collagen, gelatin, hyaluronic acid, maltodextrin, pectin, polylactic acid, polylactic acid derivatives/copolymers thereof, pullulan, scleroglucan, starch, starch derivatives, polysaccharides, dendritic polymers, polyethylene glycol, polyethylene oxide and polyvinyl alcohol.

In one embodiment, the film-forming polymer is hypromellose (HPMC). The term "hypromellose" as used herein refers to hydroxypropyl methylcellulose, CAS number 9004-65-3, E number E464. HPMC is a partly O-methylated and O-(2-hydroxypropylated) cellulose and is available in several grades that differ in molecular weight as well as in the extent of substitution, and therefore also differ in viscosity. HPMC types may be classified based on the extent of substitution, and thus given a four digit number. The first two digits refer to the percentage (w/w) of the methoxy, while the second two digits refer to the percentage of the hydroxypropoxy-groups in the dried substance. In one embodiment, the HPMC is HPMC of substitution type 2910 (also known as "E").

The structure of the HPMC, including the size and extent of substitution, gives rise to viscoelastic properties. In addition to the substitution pattern, the different HPMC grades can be distinguished by the apparent viscosity (mPas) of a 2% (w/w) aqueous solution. In one embodiment, the HPMC component has a viscosity of at least 1 mPas, such as about 3 mPas, such as about 4 to 5 mPas, such as about 5 mPas, such as at least 10 mPas, such as about 15 mPas, such as about 50 mPas. In one embodiment, the HPMC component has a viscosity of no more than 100 000 mPas, such as no more than 15 000 mPas, such as n more than 5 000 mPas, such as no more than 1 000 mPas, such as no more than 500 mPas, such as no more than 100 mPas.

As used herein, "HPMC Pharmacoat 603" refers to Hypromellose 2910, 3 mPas. As used herein, "HPMC Metolose 60SH-50" refers to Hypromellose 2910, 50 mPas, for example with 28-30% methoxy content, 7-12% hydroxypropoxy content.

In one embodiment, the HPMC is HPMC Pharmacoat 603. In one embodiment, the HPMC is HPMC Metolose 60SH-50. In one embodiment, the film-forming polymer is a mixture of HPMC Pharmacoat 603 and HPMC Metolose 60SH-50. In one embodiment, the unit dosage form comprises HPMC Pharmacoat 603 and HPMC Metolose 60SH-50 in the ratio of 70:30 to 30:70, such as 60:40, such as 50:50, such as 40:60.

In one embodiment, the film-forming polymer is alginate selected from the group consisting of sodium alginate, potassium alginate, ammonium alginate, calcium alginate, propylene glycol alginate, alginic acid and mixtures thereof. In one embodiment, the alginate is sodium alginate, potassium alginate or ammonium alginate, or a mixture thereof. In one embodiment, one or more of these alginate salts comprises from 25 to 35 wt % by weight of α-D-mannuronate and/or from 65 to 75 wt % by weight of α-L-guluronate, and a mean molecular weight of from 30,000 g/mol to 90,000 g/mol.

In one embodiment, the film-forming polymer is acrylate selected from acrylic polymers and co-polymers thereof; polyacrylic acids, polymethacrylates and co-polymers thereof (such as Eudragit E PO); and polyvinyl alcohol-polyethylene glycol graft-copolymers (for example Kollicoat, such as Kollicoat IR, which is a polymer consisting essentially of 75% polyvinyl alcohol units and 25% polyethylene glycol units)

In one embodiment, the film-forming polymer is gum selected from the group consisting of acacia gum, guar gum, tragacanth gum, xanthan gum and diutan gum.

In one embodiment, the unit dosage form comprises at least 35 wt % film-forming polymer, such as at least 45 wt %, such as at least 50 wt %, such as at least 55 wt %, such as at least 60 wt %, such as at least 65 wt % film-forming polymer.

In one embodiment, the unit dosage form comprises no more than 80 wt % film-forming polymer, such as no more than 70 wt % such as no more than 65 wt %, such as no more than 60 wt %, such as no more than 55 wt %, such as no more than 50 wt %, such as no more than 45 wt % film-forming polymer.

In one embodiment, the unit dosage form comprises 35 to 70 wt % film-forming polymer, such as 45 to 70 wt %, such as 50 to 60 wt %, such as 55 to 65 wt % film-forming polymer. In one embodiment, the unit dosage form comprises 35 to 70 wt % HPMC, such as 45 to 70 wt %, such as 50 to 65 wt %, such as 55 to 60 wt % HPMC.

In one embodiment, the ratio of Hypromellose 2910, 3 mPa·s and Hypromellose 2910, 50 mPa·s is 4:1 to 1:4, such as 3:1 to 1:3; such as 2:1 to 1:2, such as about 1:1.

Plasticizer

The mechanical properties of the film must allow for a continuous coating process and converting process, the latter of which can be rather high speed and requires strength and plasticity of the polymer-based film. One way to achieve a satisfactory plasticity is to add one or more plasticizers. In general, the optimal type and concentration of plasticizer(s) depends on a range of factors, such as the type and concentration of polymer(s). The type and concentration of API, as well as its state also have an impact when selecting optimal type and concentration of plasticizer(s), at least if the substance constitutes a significant fraction of the finished film e.g. more than 10 wt %.

Preferably, the unit dosage form of the present invention comprises an API, a film-forming polymer and one or more plasticizer(s). Plasticizers might be defined as small low molecular weight, non-volatile compounds added to polymers to reduce brittleness, impart flexibility, and enhance toughness for films.

In one embodiment, the plasticizer is selected from the group consisting of glycerol; glycerol monoacetate; citric acid and esters thereof such as triethyl citrate (TEC); diethylene glycol; ethylene glycol; fatty acid esters; PEG, such as PEG 400, PEG 600 or PEG 4000; polyethylene-propylene glycols; propylene glycol; phthalic acid; polyalkylene oxides; sorbitol, triacetin and xylitol. In one embodiment, the plasticizer is glycerol. In one embodiment, the plasticizer is TEC. In one embodiment, the plasticizer is poloxamer 407. Poloxamer 407 is a triblock copolymer consisting of a central hydrophobic block of polypropylene glycol flanked by two hydrophilic blocks of polyethylene glycol (PEG). The approximate lengths of the two PEG blocks is 101 repeat units, while the approximate length of the propylene glycol block is 56 repeat units. Thus, poloxamer 407 is a polypropylene glycol-polyethylene glycol copolymer. Poloxamer 407 is also known as Pluronic F-127, Synperonic PE/F 127 and Kolliphor P 407. In one embodiment, the plasticizer is Kollicoat IR. Kollicoat IR is a polymer comprising about 75% polyvinyl alcohol units and about 25% polyethylene glycol units, and optionally about 0.3% colloidal anhydrous silica. Thus, Kollicoat IR is a polyvinyl alcohol-polyethylene glycol copolymer. In one embodiment, the plasticizer is selected from the group consisting of glycerol; glycerol monoacetate; citric acid and esters thereof such as triethyl citrate (TEC); diethylene glycol; ethylene glycol; fatty acid esters; PEG, such as PEG 400, PEG 600 or PEG 4000; polyethylene-propylene glycols; propylene glycol; phthalic acid; polyalkylene oxides; sorbitol, triacetin and xylitol.

In one embodiment, the unit dosage form does not comprise any plasticizer. In one embodiment, the unit dosage form comprises 3 wt % plasticizer. In one embodiment, the unit dosage form comprises more than 3 wt % but less than 5 wt % plasticizer. In one embodiment, the unit dosage form comprises less than 5 wt % plasticizer, such as about 3 to 4 wt % plasticizer. In one embodiment, the unit dosage form comprises at least 3 wt % plasticizer, such as at least 5 wt %, such as at least 10 wt %, such as at least 30 wt % plasticizer. In one embodiment, the unit dosage form comprises no more than 30 wt % plasticizer, such as no more than 20 wt %, such as no more than 15 wt %, such as no more than 10 wt % plasticizer. In one embodiment, the unit dosage form comprises 3 to 35 wt % plasticizer, such as 4 to 10 wt %, such as about 5 wt % plasticizer.

In one embodiment, the unit dosage form comprises a combination of two plasticizers, for which the total concentration is equal to any of the levels presented above. In one embodiment, said two plasticizers are selected from the group consisting of glycerol, TEC, poloxamer 407 and Kollicoat IR, such as glycerol and TEC, or glycerol and poloxamer 407, or glycerol and Kollicoat IR, or TEC and poloxamer 407, or TEC and Kollicoat IR, or poloxamer 407 and Kollicoat IR.

Additives

In one embodiment, the unit dosage form further comprises one or more additives, for example a colorants, such as a pigment, and/or flavouring agents.

In one embodiment, the unit dosage form comprises an API, one or more film-forming polymers, a pigment but no other additives or excipients.

In one embodiment, the pigment is yellow iron oxide.

In one embodiment, the unit dosage form comprises at least 0.2 wt % pigment, such as at least 0.5 wt %, such as at least 1 wt % pigment. In one embodiment, the unit dosage form comprises no more than 10 wt % pigment, such as no more than 5 wt %, such as no more than 2 wt %, such as no more than 1 wt % pigment. In one embodiment, the unit dosage form comprises 0.5 to 5 wt % pigment, such as about 1 wt % pigment.

Total Composition

In one embodiment, the unit dosage form comprises 15 to 35 wt % API and 35 to 70 wt % film-forming polymer, such as 20 to 35 wt % API and 45 to 70 wt % film-forming polymer.

In one embodiment, the unit dosage form comprises 15 to 35 wt % API, 35 to 70 wt % film-forming polymer and 3 to 35 wt % plasticizer.

In one embodiment, the unit dosage form comprises 15 to 35 wt % midazolam, 35 to 70 wt % HPMC and 3 to 15 wt % glycerol. In one embodiment, the unit dosage form comprises 30 to 35 wt % midazolam, 50 to 60 wt % HPMC and 3 to 8 wt % glycerol. In one embodiment, the unit dosage form comprises about 31 to 35 wt % midazolam, 60 to 64 wt % HPMC and 3 to 7 wt % glycerol. In one embodiment, the unit dosage form comprises about 33 wt % midazolam, 61 wt % HPMC and 5 wt % glycerol. In one embodiment, the unit dosage form comprises about 33 wt % midazolam, about 63 wt % HPMC and 4 wt % glycerol.

In one embodiment, the unit dosage form comprises:
a) at least 20 wt % midazolam or a pharmaceutically acceptable salt thereof;
b) 35 to 70 wt % HPMC, wherein the HPMC is a mixture of:
   i. Hypromellose 2910, 3 mPa·s; and
   ii. Hypromellose 2910, 50 mPa·s; and
c) 3 to 8 wt % plasticizer, such as glycerol.

In one embodiment, the unit dosage form comprises 33 wt % midazolam or a pharmaceutically acceptable salt thereof, 61 wt % HPMC, 5 wt % glycerol, 1 wt % yellow iron oxide. In one embodiment, the unit dosage form consists essentially of about 33 wt % midazolam or a pharmaceutically acceptable salt thereof, 61 wt % HPMC, 5 wt % glycerol, 1 wt % yellow iron oxide.

The amounts of the various components of the unit dosage form or the film are sometimes given as wt %. In such cases, the sum of the wt % of the components does not exceed 100 wt %.

Size

Key features for oral films are that they are thin, e.g. 50-150 μm in order to achieve relatively high dissolution rate and being flexible, and that they have a feasible area that fits into the oral cavity surfaces, e.g. <5 cm², yet large enough for convenient handling e.g. >2 cm².

In one embodiment, the oral film is 30 to 150 μm thick, such as 50 to 120 μm thick, such as 70 to 110 μm thick. The thickness of an oral film is often measured and defined by coat weight, rather than being measured as an actual thickness and presented in μm. Coat weight is the weight of the dry film per unit area, and is often measured and presented as g/m². If the density of the dry film is 1 g/cm³, the numerical values of thickness in μm will equal that of coat weight in g/m².

In one embodiment, the unit dosage form has a dimension of X×Y×Z, wherein X is in the range of 0.5 to 5 cm; Y is in the range of 0.5 to 5 cm; and Z is in the range of 15 to 150 μm.

In one embodiment, X is at least 0.5 cm, such as at least 1 cm, such as at least 1.5 cm, such as at least 2 cm. In one embodiment, X is no more than 5 cm, such as no more than 4.5 cm, such as no more than 4 cm, such as no more than 3.5 cm, such as no more than 3 cm. In one embodiment, X is in the range of 0.5 to 5 cm, such as in the range of 1 to 3 cm, for example in the range of 1 to 2 cm.

In one embodiment, Y is at least 0.5 cm, such as at least 1 cm, such as at least 1.5 cm, such as at least 2 cm. In one embodiment, Y is no more than 5 cm, such as no more than 4.5 cm, such as no more than 4 cm, such as no more than 3.5 cm, such as no more than 3 cm. In one embodiment, Y is in the range of 0.5 to 5 cm, such as in the range of 1 to 3 cm, for example in the range of 2 to 3 cm.

In one embodiment, Z is at least 5 μm, such as at least 25 μm, such as at least 50 μm, such as at least 75 μm, such as at least 100 μm. In one embodiment, Z is no more than 1 mm, such as no more than 750 μm, such as no more than 500 μm, such as no more than 250 μm, such as no more than 125 μm. In one embodiment, Z is in the range of 5 μm to 750 μm, such as in the range of 30 to 150 μm, such as 50 to 120 μm, such as 70 to 110 μm.

In one embodiment, X is in the range of 0.5 to 5 cm; Y is on the range of 0.5 to 5 cm; and Z is in the range of 30 μm to 150 μm. In one embodiment, X is in the range of 1 to 3 cm; Y is on the range of 1 to 3 cm; and Z is in the range of 50 μm to 150 μm.

In one embodiment, the unit dosage form has a dimension of about 1.5 cm×2.5 cm×90 μm.

In one embodiment, the unit dosage form has an area, i.e. X×Y, of 1 to 6 cm², such as 1.5 to 5 cm², such as 3 to 4.5 cm², such as 3.5 to 4 cm².

In one embodiment has a coat weight of 50 to 150 g/m², such as 75 to 125 g/m², such as 80 to 110 g/m², such as about 90 g/m².

In one embodiment, the unit dosage form has an area of 1 to 6 cm², such as 1.5 to 5 cm², such as 3 to 4.5 cm², such as 3.5 to 4 cm², and is 30 to 150 μm thick, such as 50 to 120 μm thick, such as 70 to 110 μm thick.

In one embodiment, the unit dosage form has an area, i.e. X×Y, of 1 to 6 cm², such as 1.5 to 5 cm², such as 3 to 4.5 cm², such as 3.5 to 4 cm², and a coat weight of 50 to 150 g/m², such as 75 to 125 g/m², such as 80 to 110 g/m², such as about 90 g/m².

In one embodiment, the unit dosage form consists of a single layer.

In one embodiment, the film is homogenous.

Manufacturing Process

There are several principles for preparing and manufacturing oral films, for example described in U.S. Pat. No. 11,173,114 B1 and by Kathpalia 2013. The most common principle is the solvent casting method which can be summarized as:
1) One or more water-soluble, film-forming polymers are dissolved in water;
2) Other excipients and the active pharmaceutical ingredient (API) are added, either as dissolved or suspended in the mix which can now be called "the wet mix";
3) The wet mix is cast onto an inert release liner as a wet film, with typical thickness of 100-500 micrometer;
4) The wet mix is dried until an essentially water-free dry film is obtained, with typical thickness of 30-150 micrometer though that depends on the thickness of the wet film and the dry content of the wet mix;

5) Said film is cut into unit dose pieces and packaged into air- and water-tight pouches which become the primary containers.

As for excipients other than the film-forming polymer (which may be HPMC, PVA, alginate or a wide range of others), several excipients can be imagined: plasticizers (e.g. glycerol), fillers, colorants, flavours, disintegration agents, solubilizing agents, etc.

There are variants of this process, for example, that other volatile solvents are used alone or as co-solvents with water, or that the order between or in step 1-2 is different from above, or that multilayer films are made, that the active substance is added in an intermediate product already processed, etc.

The difference in step 2 between "dissolved" and "suspended" is essential, especially for the API because it will determine the state of the active substance inside the finished dry film, and thereby determine critical attributes such as dissolution rates and stability. As used herein, the term "suspended API" refers to an API in solid state inside the film.

In one aspect, the present invention relates to a process for producing an oral film as described herein, said process comprising the steps of:

a) mixing the API and the film-forming polymer in a process solvent to provide a wet mix solution; and b) casting the wet mix obtained in step a) to provide a final film.

In one aspect, the present invention relates to a process for producing an oral film as described herein, said process comprising the steps of:

a) mixing the API and the film-forming polymer in a solvent to provide a homogeneous wet mix in which the API is dissolved; and b) casting the wet mix obtained in step a), drying it to provide a final, dry film in which the API is still dissolved.

In one embodiment, step a) comprises the steps of:

a) dissolving the API in process solvent to obtain a homogenous solution;

b) optionally adding a plasticizer and/or a pigment to the solution in a) and mixing to obtain a homogenous solution; and c) adding the film-forming polymer to the solution and mixing to obtain the wet mix.

In another embodiment, step a) comprises the steps of:

a) mixing the film-forming polymer in process solvent to obtain a homogenous solution;

b) adding the API and optionally a plasticizer and/or a pigment to the solution in a) and mixing to obtain the wet mix.

In one embodiment, step b) comprises the steps of:

a) coating the wet mix onto an inert intermediate layer, thus forming a wet film;

b) drying the wet film; and c) removing the intermediate layer to provide the final film.

In one aspect, the present invention provides a process for producing a unit dosage form as defined herein, said process comprising the steps of a) preparing the film according to the process outlined herein; and b) cutting the final film into one or more unit dosages.

In one embodiment, the pH of the wet mix is adjusted to pH 1.5 to 2.4, such a pH 2.2, before or during the addition of the API. The aim of this is to ensure that the API remains in the dissolved state.

In one embodiment, the process solvent comprises or consists of water; volatile, polar, organic solvents; or mixtures thereof. In one embodiment, the process solvent comprises or consists of water, alcohol or mixtures thereof. In one embodiment, the solvent is a mixture of water and ethanol. In one embodiment, the ratio of water and ethanol is 70:30 to 30:70, such as 60:40 to 40:60, such as about 45:55, such as about 50:50, such as about 55:45. In one embodiment, the process solvent is volatile. The aim of using ethanol or other volatile, polar organic solvents is to ensure that the API remains in the dissolved state.

In one embodiment, the ratio of water and ethanol is between 60:40 to 40:60 and a pH adjustment is made to achieve pH 1.5 to 2.4 in the wet mix or in any of the liquid states preceding the final preparation of the wet mix. The aim of this is to ensure that the API remains in the dissolved state. In one embodiment, the API in the wet mix being subjected to those steps is midazolam. In one embodiment, the API in the wet mix is midazolam hydrochloride. In one embodiment, the API in the wet mix is midazolam maleate.

In one embodiment, the wet film thickness is 300 to 800 µm, such as 400 to 700 µm, such as 550 to 650 µm.

In one embodiment, the wet film is dried until the residual ethanol content is no more than 5 wt %, such as no more than 4 wt %, such as no more than 3 wt % such as no more than 2 wt %, such as no more than 1 wt %.

In one embodiment, the drying is performed at 80 to 110° C. In one embodiment, the drying is performed by using several temperature zones, for example, first moving the film in a zone with 80° C., the moving it into another zone with 95° C., etc.

In one embodiment, the intermediate layer is an inert, strong, flexible polymer material such as PET.

In one embodiment, the process is used for preparing a film comprising midazolam as API. In one embodiment, midazolam is added as the midazolam hydrochloride salt. In another embodiment, midazolam is added as midazolam maleate.

In one aspect, the present invention relates to a process for preparing a film comprising an API and a film-forming polymer for buccal administration comprising the steps of:

a) dissolving the API in a process solvent;

b) optionally adding a plasticizer and/or a pigment to the solution of a);

c) adding a film-forming polymer to the solution of a) or b) forming a wet mix;

d) coating the wet mix onto an intermediate layer thus forming a wet film;

e) drying the wet film to obtain a final dry film.

In one aspect, the present invention relates to a film or a unit dosage form obtainable by the process as described herein.

Biological Activity and Medical Use

In one aspect, the present invention relates to a unit dosage form as described herein for use as a medicament.

In one aspect, the present invention relates to a unit dosage form as described herein for use in the acute treatment of seizures in a subject. In one embodiment, the seizures are caused by epilepsy or another disease or condition that may cause seizures.

In one embodiment, the subject is suffering from epilepsy or another disease or condition that may cause seizures.

In one embodiment, the epilepsy is generalised epilepsy or partial epilepsy.

In one embodiment, the disease or condition that may cause seizures is selected from the group consisting of fever caused by malaria, fever of other causes, poisoning, tetanus, brain tumours, Lennox-Gastaut syndrome, tuberous sclerosis complex and Dravet syndrome.

In one embodiment, the seizures are selected from the group consisting of cluster seizures, seizure convulsions, convulsions, spasms, prolonged acute convulsive seizures, stereotypic episodes of frequent seizure activity that are distinct from a patient's usual seizure pattern, status epilepticus and convulsive refractory status epilepticus.

In one embodiment, the seizures are ongoing, acute seizures.

In one embodiment, the unit dosage form used for such treatment of various seizures is a buccal film.

In one embodiment, the unit dosage form used for such treatment of various seizures is an orodispersible film or a sublingual film.

In one embodiment, this unit dosage form is being used to treat patients with typically exhibits a behaviour—when suffering from a seizure—which means that they are drooling and/or swallowing saliva. In that embodiment, the loss of API dose due to that behaviour is reduced by the use of this unit dosage form, if compared with being treated with the same dose in the form of a buccal solution.

In one aspect, the present invention relates to a unit dosage form as described herein for use in moderate sedation before diagnostic, therapeutic or surgical procedures or pre-sedation before anaesthesia. In one embodiment, the diagnostic, therapeutic or surgical procedures include but it limited to these kind of procedures within odonthology.

In one aspect, the present invention relates to use of a unit dosage form as described herein in moderate sedation before diagnostic, therapeutic or surgical procedures or pre-sedation before anaesthesia.

In one embodiment, the unit dosage form used for such moderate or pre-sedation is an orodispersible film.

In one embodiment, the unit dosage form used for such moderate or pre-sedation is a buccal film or a sublingual film.

In one embodiment, the subject is a mammal, such a human. In one embodiment, the subject is a dog, a horse or a cat.

In one aspect, the present invention relates to a method of treating seizures in a subject, said method comprising administering the unit dosage form as described herein.

In one aspect, the present invention relates to the use of the unit dosage form as described herein in the manufacture of a medicament for use in the acute treatment of seizures in a subject.

In one aspect, the present invention relates to a method for sedation before diagnostic, therapeutic or surgical procedures or pre-sedation before anaesthesia, said method comprising administering the unit dosage form as described herein to a subject in need thereof.

In one aspect, the present invention relates to the use of the unit dosage form as described herein in the manufacture of a medicament for use in sedation before diagnostic, therapeutic or surgical procedures or pre-sedation before anaesthesia in a subject.

In one aspect, the present invention relates to a method for buccal administration of midazolam, said method comprising administering a unit dosage form as described herein.

Bioavailability

Figure 2:
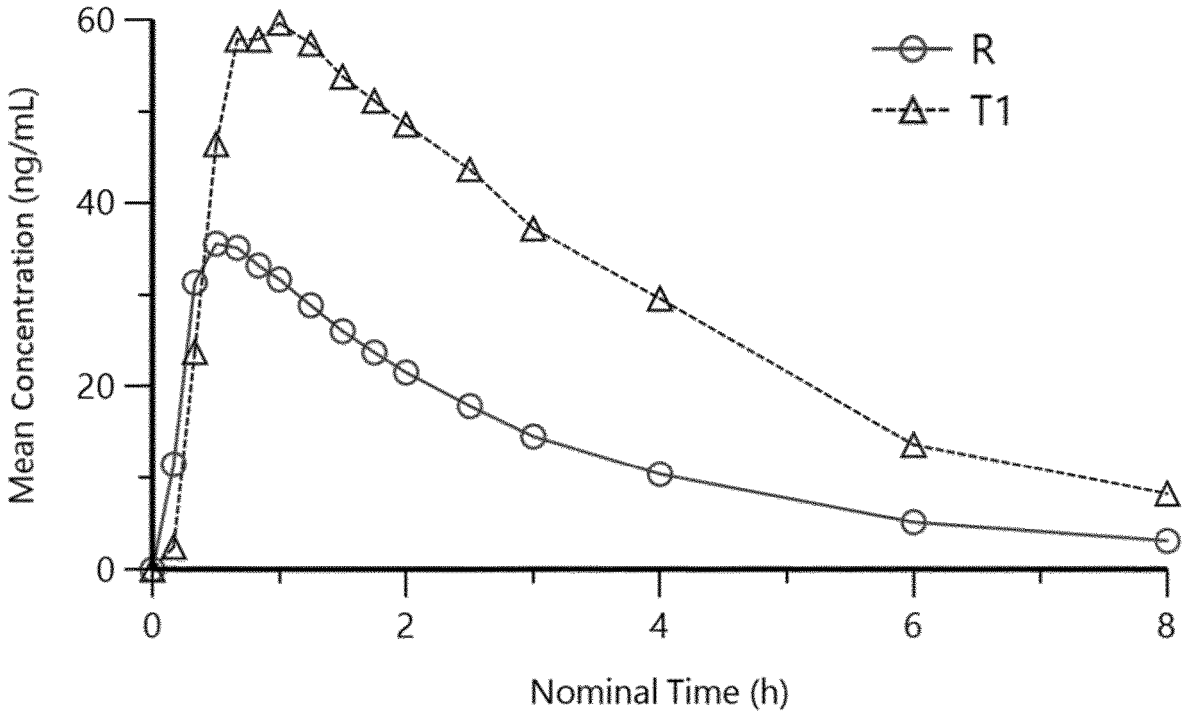
FIG. 2. Results from human bioavailability study. The curves present mean values of the 24 study subjects' plasma concentrations of midazolam (in ng/mL), versus time. T1 (triangles) represent plasma concentrations after unilateral administration of a 10 mg dose of formulation A13. R (circles) represent plasma concentrations after bilateral administration of a 10 mg dose of Buccolam oromucosal solution.

In a preferred embodiment, the unit dosage form is a buccal film. Example 11 describes a human bioavailability study of a unit dosage form of the present invention comprising 10 mg midazolam. It was found that the unit dosage form of the present invention was superior to that of a commercially available buccal solution (BUCCOLAM, with 10 mg midazolam) (FIG. 2). Thus, in one embodiment, the total drug exposure across time, for example measured as area under the curve (AUC) of the API, such as midazolam, is higher for the unit dosage form of the present invention than for a corresponding buccal solution of the API. In one embodiment, AUC is at least 25% higher for the unit dosage form of the present invention compared to a corresponding buccal solution, such as at least 50% higher, such as at least 75% higher.

In one embodiment, the maximum serum concentration, for example measured as $C_{max}$, achieved for the API, such as midazolam, is higher for the unit dosage form of the present invention than for a corresponding buccal solution of the API. In one embodiment, $C_{max}$ is at least 25% higher for the unit dosage form of the present invention compared to a corresponding buccal solution, such as at least 50% higher, such as at least 75% higher.

In one embodiment, the film provides a plasma drug concentration-time profile of midazolam, or a pharmaceutically acceptable salt thereof, where the mean $C_{max}$ is about 80% to about 125%, such as 80.00% to 125.00%, of 64.32 ng/mL (CV 7.05) after administration with a single unit dosage form comprising 10 mg midazolam (defined as base) applied on the buccal mucosa of the inside of one cheek.

In one embodiment, the film provides a plasma drug concentration-time profile of midazolam, or a pharmaceutically acceptable salt thereof, where the mean $C_{max}$ is 50 to 85 ng/mL, such as 60 to 70 ng/mL, such as 63 to 66 ng/mL, such as about 64 ng/mL after administration with a single unit dosage form comprising 10 mg midazolam (defined as base) applied on the buccal mucosa of the inside of one cheek.

In one embodiment, the film provides a plasma drug concentration-time profile of midazolam, or a pharmaceutically acceptable salt thereof, where the mean $AUC_{0-t}$ is about 80% to about 125%, such as 80.00% to 125.00%, of 223.65 ng*h/mL (CV 5.33%) after administration with a single unit dosage form comprising 10 mg midazolam (defined as base) applied on the buccal mucosa.

In one embodiment, the film provides a plasma drug concentration-time profile of midazolam, or a pharmaceutically acceptable salt thereof, where the mean $AUC_{0-t}$ is 175 to 280 ng*h/mL, such as 200 to 250 ng*h/mL, such as 220 to 225 ng*h/mL, such as about 224 ng*h/mL after administration with a single unit dosage form comprising 10 mg midazolam (defined as base) applied on the buccal mucosa.

In one embodiment, the film provides a plasma drug concentration-time profile of midazolam, or a pharmaceutically acceptable salt thereof, where the mean $T_{max}$ is 0.25 to 2.5 h, such as 0.5 to 2 h, such as 0.75 to 1.5 h, such as about 1 h after administration with a single unit dosage form comprising 10 mg midazolam (defined as base) applied on the buccal mucosa.

In one embodiment, $C_{max}$, $AUC_{0-t}$ and $T_{max}$ are after administration with a single unit dosage form comprising 10 mg midazolam (defined as base) applied on the buccal mucosa of a healthy, human, male study subject of 18-55 years age and a BMI of 18.5-30 kg/m.

Items

1. A unit dosage form in the form of an oral film comprising an active pharmaceutical ingredient (API) and one or more film-forming polymers.

2. The unit dosage form according to item 1, wherein the film has medium-to-high dissolution rate for the rapid delivery of API into systemic circulation.

3. The unit dosage form according to any one of the preceding items, wherein the film is an orodispersible film.

4. The unit dosage form according to any one of items 1 or 2, wherein the film is a buccal film.

5. The unit dosage form according to any one of the preceding items, wherein the film is a mucoadhesive film.

6. The unit dosage form according to any one of the preceding items, wherein the API is capable of providing relief from ongoing seizures.

7. The unit dosage form according to any one of the preceding items, wherein the API has a sedative effect.

8. The unit dosage form according to any one of the preceding items, wherein the API is selected from the group consisting of benzodiazepines and benzodiazepine-like substances.

9. The unit dosage form according to any one of the preceding items, wherein the API is selected from the group consisting of midazolam, diazepam, alprazolam, brotizolam, cinolazepam, clizolam, clobazam, clonazepam, clonazolam, clorazepate, cloxazolam, diclazepam, estazolam, flubromezepine, flunitrazepam, flurazepam, flutoprazepam, kvazepam, lorazepam, loprazolam, lormetazolam metizolam, nitrazepam, oxazepam, phenazepam, temazolam, triazolam and pharmaceutically acceptable salts thereof.

10. The unit dosage form according to any one of the preceding items, wherein the API is midazolam, diazepam, clobazam, clonazepam, lorazepam or a pharmaceutically acceptable salt thereof.

11. The unit dosage form according to any one of the preceding items, wherein the API is midazolam, diazepam, or a pharmaceutically acceptable salt thereof.

12. The unit dosage form according to any one of the preceding items, wherein the API is midazolam or a pharmaceutically acceptable salt thereof.

13. The unit dosage form according to any one of the preceding items, wherein the pharmaceutically acceptable salt is hydrochloride or maleate.

14. The unit dosage form according to any one of the preceding items, wherein the API is midazolam hydrochloride.

15. The unit dosage form according to any one of the preceding items, wherein the unit dosage form comprises at least 2.5 mg of API, such as at least 5 mg, such as at least 10 mg of API.

16. The unit dosage form according to any one of the preceding items, wherein the unit dosage form comprises no more than 20 mg of API, such as no more than 15 mg, such as no more than 10 mg of API.

17. The unit dosage form according to any one of the preceding items, wherein the unit dosage form comprises 2.5 to 20 mg of API, such as 5 to 15 mg, such about 10 mg, such as about 7.5 mg, such as about 5 mg of API.

18. The unit dosage form according to any one of the preceding items, wherein the unit dosage form comprises about 10 mg midazolam.

19. The unit dosage form according to any one of the preceding items, wherein the unit dosage form comprises about 7.5 mg midazolam.

20. The unit dosage form according to any one of the preceding items, wherein the unit dosage form comprises about 5 mg midazolam.

21. The unit dosage form according to any one of the preceding items, wherein the concentration of API in the film is at least 10 wt %, such as at least 15 wt %, such as at least 20 wt %, such as at least 25 wt %, such as at least 30 wt %.

22. The unit dosage form according to any one of the preceding items, wherein the concentration of API in the film is no more than 80 wt %, such as no more than 70 wt %, such as no more than 60 wt %, such as no more than 50 wt %, such as no more than 40 wt %.

23. The unit dosage form according to any one of the preceding items, wherein the concentration of API in the film is in the range of 10 to 60 wt %, such as in the range of 15 to 40 wt %, such as in the range of 15 to 25 wt % or such as in the range of 30 to 60 wt %, for example in the range of 20 to 40 wt %, such as in the range of 25 to 35 wt %, such as in the range of 30 to 35 wt %.

24. The unit dosage form according to any one of the preceding items, wherein the API is predominately in dissolved state in the film.

25. The unit dosage form according to any one of the preceding items, wherein at least 60 wt %, such as at least 70 wt %, such as at least 80 wt %, such as at least 90 wt %, such as at least 95 wt %, such as at least 98 wt % of the API is in dissolved state in the film.

26. The unit dosage form according to any one of the preceding items, wherein the concentration of API in the film is in the range of 15 to 35 wt % and at least 60 wt %, such as at least 70 wt %, such as at least 80 %, such as at least 90 wt %, such as at least 95 wt %, such as at least 98 wt % of the API is in dissolved state in the film.

27. The unit dosage form according to any one of the preceding items, wherein the film-forming polymer is selected from the group consisting of HPMC, alginate, acrylate, PVP, gum, carrageenan, chitosan, collagen, gelatin, hyaluronic acid, maltodextrin, pectin, polylactic acid, polylactic acid derivatives/copolymers thereof, pullulan, scleroglucan, starch, starch derivatives, polysaccharides, dendritic polymers, polyethylene glycol, polyethylene oxide and polyvinyl alcohol.

28. The unit dosage form according to any one of the preceding items, wherein the film-forming polymer is HPMC.

29. The unit dosage form according to item 28, wherein the HPMC is of substitution type 2910.

30. The unit dosage form according to item 27, wherein the alginate is selected from the group consisting of sodium alginate, potassium alginate, ammonium alginate, calcium alginate, propylene glycol alginate, alginic acid and mixtures thereof.

31. The unit dosage form according to item 30, wherein the alginate is sodium alginate, potassium alginate or ammonium alginate, or a mixture thereof, wherein one or more of these alginate salts comprises from 25 to 35 wt % by weight of $\alpha$-D-mannuronate and/or from 65 to 75 wt % by weight of $\alpha$-L-guluronate, and a mean molecular weight of from 30,000 g/mol to 90,000 g/mol.

32. The unit dosage form according to item 27, wherein the acrylate is selected from acrylic polymers and co-polymers thereof, polyacrylic acids, and polymethacrylates such as Eudragit and Kollicoat, for example Kollicoat IR.

33. The unit dosage form according to item 27, wherein the gum is selected from the group consisting of acacia gum, guar gum, tragacanth gum, xanthan gum and diutan gum.

34. The unit dosage form according to any one of the preceding items, wherein the unit dosage form comprises at least 35 wt % film-forming polymer, such as at least 45 wt %, such as at least 50 wt %, such as at least 55 wt %, such as at least 60 wt %, such as at least 65 wt % film-forming polymer.

35. The unit dosage form according to any one of the preceding items, wherein the unit dosage form comprises no more than 80 wt % film-forming polymer, such as no more than 70 wt % such as no more than 65 wt %, such as no more than 60 wt %, such as no more than 55 wt %, such as no more than 50 wt %, such as no more than 45 wt % film-forming polymer.

36. The unit dosage form according to any one of the preceding items, wherein the unit dosage form comprises 35 to 70 wt % film-forming polymer, such as 45 to 70 wt %, such as 50 to 60 wt %, such as 55 to 65 wt % film-forming polymer.

37. The unit dosage form according to any one of the preceding items, wherein the unit dosage form comprises 15 to 35 wt % API and 35 to 70 wt % film-forming polymer, such as 20 to 35 wt % API and 45 to 70 wt % film-forming polymer.

38. The unit dosage form according to any one of the preceding items, further comprising one or more plasticizer.

39. The unit dosage form according to item 38, wherein the plasticizer is selected from the group consisting of glycerol; glycerol monacetate; citric acid and esters thereof such as triethyl citrate (TEC); diethylene glycol; ethylene glycol; fatty acid esters; PEG, such as PEG 400, PEG 600 or PEG 4000; polyethylene-propylene glycols; propylene glycol; phthalic acid; polyalkylene oxides; sorbitol, triacetin and xylitol.

40. The unit dosage form according to item 38, wherein the plasticizer is glycerol.

41. The unit dosage form according to item 38, wherein the plasticizer is TEC.

42. The unit dosage form according to any one of items 38 to 41, wherein the unit dosage form comprises at least 3 wt % plasticizer, such as at least 5 wt %, such as at least 10 wt %, such as at least 30 wt % plasticizer.

43. The unit dosage form according to any one of items 38 to 42, wherein the unit dosage form comprises no more than 30 wt % plasticizer, such as no more than 20 wt %, such as no more than 15 wt %, such as no more than 10 wt % plasticizer.

44. The unit dosage form according to any one of items 38 to 41, wherein the unit dosage form comprises 3 to 35 wt % plasticizer, such as 4 to 10 wt %, such as about 5 wt % plasticizer.

45. The unit dosage form according to item 1, wherein the unit dosage form comprises 15 to 35 wt % API, 35 to 70 wt % film-forming polymer and 3 to 35 wt % plasticizer.

46. The unit dosage form according to item 1, wherein the unit dosage form comprises 15 to 35 wt % midazolam, 35 to 70 wt % HPMC and 3 to 15 wt % glycerol.

47. The unit dosage form according to item 1, wherein the unit dosage form comprises 30 to 35 wt % midazolam, 50 to 60 wt % HPMC and 3 to 8 wt % glycerol.

48. The unit dosage form according to item 1, wherein the unit dosage form comprises about 31 to 35 wt % midazolam, 60 to 64 wt % HPMC and 3 to 7 wt % glycerol.

49. The unit dosage form according to item 1, wherein the unit dosage form comprises about 33 wt % midazolam, 62 wt % HPMC and 5 wt % glycerol.

50. The unit dosage form according to any one of the preceding items, further comprising one or more colorant, such as a pigment.

51. The unit dosage form according to item 50, wherein the pigment is yellow iron oxide.

52. The unit dosage form according to any one of the preceding items, wherein the unit dosage form comprises at least 0.2 wt % pigment, such as at least 0.5 wt %, such as at least 1 wt % pigment.

53. The unit dosage form according to any one of the preceding items, wherein the unit dosage form comprises no more than 10 wt % pigment, such as no more than 5 wt %, such as no more than 2 wt %, such as no more than 1 wt % pigment.

54. The unit dosage form according to any one of the preceding items, wherein the unit dosage form comprises 0.5 to 5 wt % pigment, such as about 1 wt % pigment.

55. The unit dosage form according to any one of the preceding items, wherein the unit dosage form comprises one or more flavouring agents.

56. The unit dosage form according to any one of the preceding items with the proviso that the sum of the wt % of the components does not exceed 100 wt %.

57. The unit dosage form according to any one of the preceding items, wherein the film is 30 to 150 μm thick, such as 50 to 120 μm thick, such as 70 to 110 μm thick.

58. The unit dosage form according to any one of the preceding items, wherein the unit dosage form has a dimension of X×Y×Z, wherein X is in the range of 0.5 to 5 cm; Y is in the range of 0.5 to 5 cm; and Z is in the range of 15 to 150 μm.

59. The unit dosage form according to any one of the preceding items, wherein X is at least 0.5 cm, such as at least 1 cm, such as at least 1.5 cm, such as at least 2 cm.

60. The unit dosage form according to any one of the preceding items, wherein X is no more than 5 cm, such as no more than 4.5 cm, such as no more than 4 cm, such as no more than 3.5 cm, such as no more than 3 cm.

61. The unit dosage form according to any one of the preceding items, wherein X is in the range of 0.5 to 5 cm, such as in the range of 1 to 3 cm, for example in the range of 1 to 2 cm.

62. The unit dosage form according to any one of the preceding items, wherein Y is at least 0.5 cm, such as at least 1 cm, such as at least 1.5 cm, such as at least 2 cm.

63. The unit dosage form according to any one of the preceding items, wherein Y is no more than 5 cm, such as no more than 4.5 cm, such as no more than 4 cm, such as no more than 3.5 cm, such as no more than 3 cm.

64. The unit dosage form according to any one of the preceding items, wherein Y is in the range of 0.5 to 5 cm, such as in the range of 1 to 3 cm, for example in the range of 2 to 3 cm.

65. The unit dosage form according to any one of the preceding items, wherein Z is at least 5 μm, such as at least 25 μm, such as at least 50 μm, such as at least 75 μm, such as at least 100 μm.

66. The unit dosage form according to any one of the preceding items, wherein Z is no more than 1 mm, such as no more than 750 μm, such as no more than 500 μm, such as no more than 250 μm, such as no more than 125 μm.

67. The unit dosage form according to any one of the preceding items, wherein Z is in the range of 5 μm to 750 μm, such as in the range of 30 to 150 μm, such as 50 to 120 μm, such as 70 to 110 μm.

68. The unit dosage form according to any one of the preceding items, wherein X is in the range of 0.5 to 5 cm; Y is on the range of 0.5 to 5 cm; and Z is in the range of 30 μm to 150 μm.

69. The unit dosage form according to any one of the preceding items, wherein X is in the range of 1 to 3 cm; Y is on the range of 1 to 3 cm; and Z is in the range of 50 μm to 150 μm.

70. The unit dosage form according to any one of the preceding items, wherein the film has a dimension of about 1.5 cm×2.5 cm×90 μm.

71. The unit dosage form according to any one of the preceding items, wherein the unit dosage form has an area of 1 to 6 cm$^2$, such as 1.5 to 5 cm$^2$, such as 3 to 4.5 cm$^2$, such as 3.5 to 4 cm$^2$.

72. The unit dosage form according to any one of the preceding items, wherein the unit dosage form has an area of 1 to 6 cm$^2$, such as 1.5 to 5 cm$^2$, such as 3 to 4.5 cm$^2$, such as 3.5 to 4 cm$^2$, and is 30 to 150 μm thick, such as 50 to 120 μm thick, such as 70 to 110 μm thick.

73. The unit dosage form according to any one of the preceding items, wherein the film has a coat weight of 50 to 150 g/m$^2$, such as 75 to 125 g/m$^2$, such as 80 to 110 g/m$^2$, such as about 90 g/m$^2$.

74. The unit dosage form according to any one of the preceding items, wherein the total weight of the unit dosage form is in the range of 10 mg to 50 mg, such as in the range of 15 mg to 40 mg, for example in the range of 25 mg to 40 mg, for example in the range of 30 mg to 40 mg.

75. The unit dosage form according to any one of the preceding items, wherein the unit dosage form consists of a single layer.

76. The unit dosage form according to any one of the preceding items, wherein the API has been dissolved within 10 minutes in the USP Dissolution Apparatus 2—Paddle, such as at least 90%, such as at least 95% of the API has been dissolved within 10 minutes.

77. The unit dosage form according to any one of the preceding items, wherein the API is midazolam and at least 85% of the midazolam has been dissolved within 10 minutes in the USP Dissolution Apparatus 2—Paddle (37° C.±0.5° C., 75 rpm in 1000 mL phosphate buffer pH 6.8), such as at least 90%, such as at least 95% of the midazolam has been dissolved within 10 minutes.

78. A process for producing a unit dosage according to any one of the preceding items, the process comprising the steps of:

a) mixing the API and the film-forming polymer in a process solvent to provide a wet mix; and b) casting the wet mix obtained in step a) to provide a final film.

79. The process according to item 78, wherein step a) comprises the steps of:

a) dissolving the API in process solvent to obtain a homogenous solution;

b) optionally adding a plasticizer and/or a pigment to the solution in a) and mixing to obtain a homogenous solution; and c) adding the film-forming polymer to the solution and mixing to obtain the wet mix.

80. The process according to item 78, wherein step a) comprises the steps of:

a) mixing the film-forming polymer in process solvent to obtain a homogenous solution;

b) adding the API and optionally a plasticizer and/or a pigment to the solution in a) and mixing to obtain the wet mix.

81. The process according to item 78, wherein step b) comprises the steps of:

a) coating the wet mix onto an inert intermediate layer, thus forming a wet film;

b) drying the wet film; and c) removing the intermediate layer to provide the final film.

82. The process according to any one of items 78 to 81, wherein the final film is cut into one or more unit dosages.

83. The process according to item 78, wherein the pH of the wet mix is adjusted to pH 1.5 to 2.4, such a pH 2.2.

84. The process according to item 78, wherein the solvent comprises or consists of water, alcohol or mixtures thereof.

85. The process according to item 84, wherein the solvent is a mixture of water and ethanol.

86. The process according to item 85, wherein the ratio of water and ethanol is 70:30 to 30:70, such as 60:40 to 40:60, such as about 45:55, such as about 50:50, such as about 55:45.

87. The process according to item 81, wherein the wet film is dried until the residual ethanol content is no more than 5 wt %, such as no more than 4 wt %, such as no more than 3 wt % such as no more than 2 wt %, such as no more than 1 wt %.

88. The process according to any one of items 78 to 87, wherein the wet film thickness is 300 to 800 μm, such as 400 to 700 μm, such as 550 to 650 μm.

89. The process according to item 81, wherein the drying is performed at 80 to 110 C.

90. The process according to item 81, wherein the intermediate layer is an inert, strong, flexible polymer material such as PET.

91. The process according to any one of items 78 to 90, wherein the midazolam is midazolam HCl salt.

92. The unit dosage form according to any one of items 1 to 77 for use as a medicament.

93. The unit dosage form according to any one of items 1 to 77 for use in the acute treatment of seizures in a subject.

94. The unit dosage form for use according to item 93, wherein the seizures are caused by epilepsy or another disease or condition that may cause seizures.

95. The unit dosage form for use according to item 93, wherein the subject is suffering from epilepsy or another disease or condition that may cause seizures.

96. The unit dosage form for use according to item 94 or 95, wherein the epilepsy is generalised epilepsy or partial epilepsy.

97. The unit dosage form for use according to item 94 or 95, wherein the disease or condition that may cause seizures is selected from the group consisting of fever caused by malaria, fever of other causes, poisoning, tetanus, brain tumours, Lennox-Gastaut syndrome, tuberous sclerosis complex and Dravet syndrome.

98. The unit dosage form for use according to any one of items 93 to 97, wherein the seizures are selected from the group consisting of cluster seizures, seizure convulsions, convulsions, spasms, prolonged acute convulsive seizures, stereotypic episodes of frequent seizure activity that are distinct from a patient's usual seizure pattern, status epilepticus and convulsive refractory status epilepticus.

99. The unit dosage form for use according to any one of items 93 to 98, wherein the seizures are ongoing, acute seizures.

100. The unit dosage form according to any one of items 1 to 77 for use in sedation before diagnostic, therapeutic or surgical procedures or pre-sedation before anaesthesia.

101. A method of treating seizures in a subject, said method comprising administering the unit dosage form according to any one of items 1 to 77.

102. Use of the unit dosage form according to any one of items 1 to 77 in the manufacture of a medicament for use in the acute treatment of seizures in a subject.

EXAMPLES

Materials

Components used in the Examples below, and their intended or hypothesized functions:

| Excipient/material | Intended function | Compendial | Supplier (Country) (Manufacturer, if other) |
|---|---|---|---|
| Midazolam hydrochloride (midazolam HCl) | Active ingredient | PhEur | Cambrex (Italy) |
| HPMC Metolose 60SH-50 | Film forming polymer | PhEur/USP/ JPE | SEPPIC (France) (ShinEtsu) |
| HPMC Pharmacoat 603 | Film forming polymer | PhEur/USP/ JPE | SEPPIC (France) (ShinEtsu) |
| HPMC Benecel E-50 | Film forming polymer | USP | Ashland (US) |
| PVA Gohsenol EG-05PW | Film forming polymer | PhEur/USP/ JPE | HARKE Pharma (Germany) (Nippon Gohsei) |
| PVA Gohsenol EG-40PW | Film forming polymer | PhEur/USP/ JPE | HARKE Pharma (Germany) (Nippon Gohsei) |
| Pullulan | Film forming polymer | PhEur | Sigma-Aldrich (Sweden) (*) |
| Glycerol 99.7% | Plasticizer | PhEur/USP | Univar (Germany) (Olin)* |
| Citric acid | Saliva stimulant | N/A* | * |
| Polysorbate 80 | Solubilizer and/or plasticizer | N/A* | * |
| Xylitol | Sweetening agent and/or plasticizer | N/A* | * |

-continued

| Excipient/material | Intended function | Compendial | Supplier (Country) (Manufacturer, if other) |
|---|---|---|---|
| Sorbitol | Sweetening agent and/or plasticizer | N/A* | Roquette (France)* |
| Corn starch | Filler or Disintegrant | N/A* | * |
| Microcrystalline cellulose (Avicel PH-105) | Filler or Disintegrant | PhEur/USP/ JPE | IMCD (UK) (FMC, Dupont) |
| Purified Water | Process solvent | PhEur | Cooper Industrie (France)* |
| Kollicoat IR | Film forming polymer, or Plasticizer | PhEur/USP | BTC (Germany) (BASF Pharma) |
| Triethyl citrate (TEC) | Plasticizer | Reagent Laboratory | Acros organics (Belgium) (Fisher Scientific) |
| Poloxamer 407 | Plasticizer | PhEur/USP/ JPE | BTC (France) (BASF) |
| Yellow iron oxide | Pigment | USP | Sensient (Germany) (IMCD) |
| Ethanol | Process solvent | PhEur | Charbonneaux Brabant (France) (Tereos)* |
| Hydrochloric acid (HCl) | pH adjusting agent | N/A* | * |
| Sodium hydroxide (NaOH ) | pH adjusting agent | N/A* | * |
| Loparex 78LC1 | Process liner | In-house | Loparex (Netherlands) |
| PET ALU PE peelable L188 | Primary packaging material | In-house | AMCOR (Belgium) |

*) For some materials, the precise quality or supplier are considered to be non-critical for the purpose of conducting the studies in these examples.

Example 1. Placebo Formulations

It was hypothesized that a buccal film for which a rapid and high systemic absorption is deemed desirable as well as biologically possible (considering its physicochemical properties) should have a relatively high dissolution rate. To achieve such relatively high dissolution rate, it was hypothesized that the drug substance should be dissolved in the film, i.e. not suspended. Likewise, the film should have a modest bioadhesivity, and not be too thick, though yet accommodating the intended dose of the API. Various placebo films were thus prepared, with the aim to identify one or more formulation concepts to progress into the development of active formulations.

Methods

Film samples were made with the following preparation procedure:

1. The ingredients, except the film forming polymer(s), were dissolved in water* in a 25 mL glass beaker, during manual mixing, until a homogeneous solution was obtained.

2. The film forming polymer(s) were added, during manual mixing, until a homogeneous viscous solution was obtained. This solution was denoted "the wet mix". The wet mix batch size was about 12 g. The dry content of the wet mix was between 18-25 wt %.

3. Using a film knife (Adjustable Micrometer Film Applicator, 1117/150 mm, from TQC Sheen, UK) a film of that wet film with thickness of about 500 µm was spread out onto a glass plate. This was made within 48 hours after preparing the wet mix. The resulting film was denoted "the wet film".

4. That wet film was dried during 20-40 minutes at 40-100° C. in a laboratory heating oven (Binder GmbH).

5. The resulting final, dry, film, which had thicknesses between 70-110 μm, was carefully removed from the glass plate, cut into film pieces of about 1.5 cm×2.5 cm. The resulting film, which was denoted the "dry film", or just "film", was then subjected to tests.

*) In some cases, some ethanol was added to facilitate the subsequent polymer dissolution and swelling Film Dissolution Rate is Assessed with the Following Procedure:

A modified version of an in vitro method described briefly by Wasilevska and Winnicka 2019 is used. In this modified method, 5 mL of water is placed in a Petri dish. The film is placed on the water surface by the help of a pincer. The clock is started and the Petri dish is gently shaken by moving it about 10 mm sideways back and forth about one time per second. The time for the first sign of film dissolution or disintegration is noted (T1), as well as the time when it is judged that the film has been dissolved to at least 90% of the area (T2). These observed times becomes the relative measure of film dissolution rate in each series of films tested, and the results are reported as 1, 2 or 3, where 1 means T1<1 minute and T2<2 minutes, and 3 means T1>2 minutes and T2>5 minutes. This assessment of film dissolution rate does not involve assessment of the drug substance dissolution and/or release, and is thus not to be confused with dissolution testing such as for example with USP Paddle method. The film dissolution rate for placebo formulations is assessed to approximately predict the film dissolution rate if such placebo films will later be modified to also contain the API Mechanical Properties are Assessed with the Following Procedures:

Folding endurance: A modified version of a method described by Wasilewska and Winnicka 2019 is used. In this modified method, one film piece is bent at least 10 times back and forth along the length axis, then another piece (from same batch) 10 times back and forth along the width axis, and finally another piece along the diagonal axis. If not breaking, the film is judged to have a good folding endurance; if breaking after three or less bendings, it is judged poor. Breaking characteristics: One film piece is manually pulled apart in as straight opposite direction as possible. When the film eventually breaks (due to the force and/or due to undeliberate skewing) the breaking line is observed. If breaking according to straight line perpendicular or close thereto, it is judged to have good breaking characteristics. If a very irregular line and/or largely non-perpendicular, it is judged poor. Overall Mechanical properties are reported as 1, 2 or 3, where 1 means the desirable outcome of not breaking within 10 bendings and breaking, after pulled apart, along a straight, perpendicular line, and 3 means breaking within 3 bendings and breaking, after pulled apart, along cracked irregular line.

Results

About 50 different film formulations were prepared, of which a representative selection is presented in the table below. The figures in rows 1-13 refer to the concentration of each component (wt %) in the resulting dry film.

|  | P1 | P2 | P3 | P4 | P5 | P6 | P7 | P8 | P9 | P10 | P11 |
|---|---|---|---|---|---|---|---|---|---|---|---|
| Formulation: |  |  |  |  |  |  |  |  |  |  |  |
| HPMC Metolose 60SH-50 |  |  |  |  |  |  | 28.3 |  | 68.9 | 21.0 |  |
| HPMC Pharmacoat 603 |  |  |  |  |  |  | 24.4 |  | 17.2 | 25.0 |  |
| HPMC Benecel E-50 | 92.9 | 100.0 | 86.0 | 84.0 | 73.0 | 65.8 |  |  |  |  |  |
| PVA Gohsenol EG-05PW |  |  |  |  |  |  |  |  |  |  | 25.0 |
| PVA Gohsenol EG-40PW |  |  |  |  |  |  |  |  |  |  | 21.0 |
| Pullulan |  |  |  |  |  |  |  | 72.7 |  |  |  |
| Glycerol | 5.7 |  | 10.0 | 11.0 | 20.0 | 20.2 | 13.9 | 8.1 | 13.9 | 14.0 | 14.0 |
| Citric acid |  |  | 4.0 |  |  |  |  |  |  |  |  |
| Polysorbate 80 | 1.4 |  |  | 5.0 |  |  |  |  |  |  |  |
| Xylitol |  |  |  |  |  | 14.0 |  |  |  |  |  |
| Sorbitol |  |  |  |  | 7.0 |  |  |  |  |  |  |
| Corn starch |  |  |  |  |  |  | 16.7 | 9.6 |  | 20.0 | 20.0 |
| Microcrystalline cellulose | | | | | | | 16.7 | 9.6 | | 20.0 | 20.0 |
| Results: |  |  |  |  |  |  |  |  |  |  |  |
| Film dissolution rate: | 2 | 3 | 2 | 3 | 2 | 2 | 1 | 1 | 1 | 1 | 1 |
| Mechanical properties | 1 | 2 | 1 | 1 | 1 | 1 | 1 | 2 | 2 | 1 | 1 |

Conclusions

It was concluded that HPMC, PVA and pullulan appear to be feasible film-forming polymers for the intended film formulation, and presumably other well-known film forming polymers, such as for example alginates or polyvinyl alcohol-polyethylene glycol graft copolymers, can also be feasible, that glycerol is a feasible plasticizer although the optimized level was not determined, and that polysorbate 80, xylitol, sorbitol or inert filler materials such as corn starch and microcrystalline cellulose do not provide any essentially different or desirable properties.

While several formulations thus appeared feasible, it was decided to continue studying active formulations based on two concepts: mixtures of Metolose 60SH-50 and HPMC Pharmacoat 603, and mixtures of PVA Gohsenol EG-05PW and PVA Gohsenol EG-40PW, respectively.

Example 2. Active Formulations Based on HPMC and PVA, Respectively

Based on the results with placebo formulation concepts in Example 1, the aim with Example 2 was to assess the effects of adding the active drug substance. The same parameters that were assessed, i.e., film dissolution rate and mechanical properties (with the same definitions, limitations and methods as in Example 1). Parameters directly related to the drug substance (drug substance release/dissolution, chemical stability, etc.) were not assessed.

Methods

The same methods as in Example 1 were used, as well as the rating of results as 1-3.

Results

Two film formulations were prepared, which are presented in the table below. The figures in rows 1-8 refer to the concentration of each component (wt %) in the resulting dry film.

| | Formulation: | |
| --- | --- | --- |
| | A1 | A2 |
| Midazolam HCl | 24.4 | 24.4 |
| HPMC Metolose 60SH-50 | 16.1 | |
| HPMC Pharmacoat 603 | 19.1 | |
| PVA Gohsenol EG-05PW | | 19.1 |
| PVA Gohsenol EG-40PW | | 16.1 |
| Glycerol | 10.1 | 10.1 |
| Corn starch | 15.2 | 15.1 |
| Microcrystalline cellulose | 15.1 | 15.1 |
| Results: | | |
| Film dissolution rate: | 1(+) | 1(+) |
| Mechanical properties | 1 | 1(+) |

Conclusions

It was concluded that these two formulation concepts (i.e. HPMC and PVA, respectively) remain viable also in the presence of the drug substance.

Example 3. Active Formulations with Higher Drug Load

It was realized that in order to achieve a strength of 10 mg midazolam (here given as base) and yet having a feasible film thickness allowing for a relatively high film dissolution (e.g. about 90 μm) and a convenient size (e.g. 1.5×2.5 cm), the concentration of midazolam HCl in the dry film must be about 33 wt %, i.e., higher than it was in Example 2.

Methods

The preparation procedure as described in Example 1 was used but with the following exceptions: before continuing with step 3, portions of the solutions obtained in step 1 and the wet mix obtained in step 2, respectively, were set aside for being separately studied later. Film dissolution rate or mechanical properties were not assessed. Instead, focus was on microscopic studies of the solution (step 1), the wet mix (step 2) and the film (step 5). Normal light microscopy as well as cross-polarized light microscopy were used.

The figures in rows 1-7 refer to the concentration of each component (wt %) in the resulting dry film, and rows 8-10 refer to the wet mix.

| | Formulation: | |
| --- | --- | --- |
| | A3 | A4 |
| Midazolam HCl | 34.9 | 33.1 |
| HPMC Metolose 60SH-50 | 17.3 | |
| HPMC Pharmacoat 603 | 20.5 | |
| PVA Gohsenol EG-05PW | | 28.7 |
| PVA Gohsenol EG-40PW | | 23.8 |
| Glycerol | 11.0 | 14.4 |
| Microcrystalline cellulose | 16.2 | |
| Wet mix batch size | 12 g | 25 g |
| Dry content of wet mix | 28 wt % | 30 wt % |
| Midazolam HCl in wet mix | 9.8 wt % | 9.9 wt % |

Results

It was found that the midazolam HCl first dissolved rapidly in the solution in step 1, as expected and previously observed. However, when the solution portion set aside was observed, after 30 minutes, this solution was not clear. Using light microscopy and cross-polarized light microscopy, the occurrence of particles was observed. Particles were also observed in the wet mix (step 2) and the finished dry films (step 5). It was believed that the particles consisted wholly or partly of precipitated midazolam although the exact composition or structure was not determined.

Conclusions

It was concluded:

that despite the high dissolution rate and the high apparent solubility of midazolam HCl in water, a clear, stable, particle-free solution is not obtained when dissolving high levels (e.g., >6 wt %) of midazolam HCl in water, therefore, a significant fraction of the added midazolam HCl may eventually occur as particles in the film which is not desirable, and that solving this problem by significantly lowering the midazolam HCl concentration in the wet mix, for example to 2.5 wt %, is not an option due to the targets and limitations with regard to dry content in wet mix and the eventual drug load in the dry film.

It was decided to study these challenges before continuing with the search for an optimal film formulation.

Example 4. Solutions Containing Midazolam HCl

Solutions were prepared with the aim to obtain clear, stable, particle-free solutions containing high levels of dissolved midazolam HCl. It was hypothesized that this could be achieved by lowering the pH and/or by using a co-solvent such as for example ethanol.

Methods

Visual observation, microscopy and a pH meter were used to assess the results.

Results

Study of the pH approach: An aqueous solution containing 8.9 wt % midazolam HCl and 4.8 wt % glycerol was prepared. Initially the midazolam appeared to dissolve but a clear stable solution was never obtained. Instead it became a suspension, which had pH3.34. Droplets of 1M HCl was added until a clear stable solution was obtained. That solution had pH1.84. The solution was back-titrated with droplets of 10M NaOH until a precipitation started to occur again, which happened at pH2.76. The study was repeated with a new solution of the same composition, and the results were pH2.94, pH2.00 and pH2.56, respectively.

Study (1) of the ethanol approach: Three wet mixes of about 50 mL were prepared according to the table below. The figures in rows 1-5 refer to wt % in the wet mix, and row 6 describes the solvent composition. No particles were observed in any of WM1, WM2 or WM3.

| | Wet mix preparation: | | |
| | WM1 | WM2 | WM3 |
|---|---|---|---|
| Midazolam HCl | 7.17 | 7.17 | 7.17 |
| HPMC Metolose 60SH-50 | 5.22 | 5.22 | 5.22 |
| HPMC Pharmacoat 603 | 6.30 | 6.30 | 6.30 |
| Glycerol | 3.04 | 3.04 | 3.04 |
| Ethanol:water solvent | 78.26 | 78.26 | 78.26 |
| Ethanol wt % in that solvent | 80 | 60 | 50 |

Study (2) of the ethanol approach: Three wet mixes of about 50 mL were prepared according to the table below. The figures in rows 1-5 refer to wt % in the wet mix, and row 6 describes the solvent composition. Visual observation and microscopy were used to study the resulting wet mixes after preparation, and also after 3 days. After the observation at Day 3, the wet mixes was put into an oven of 50° C., with no cover, and were thus allowed to evaporate.

| | Wet mix preparation: | | |
| | WM4 | WM5 | WM6 |
|---|---|---|---|
| Midazolam HCl | 7.10 | 7.10 | 7.10 |
| HPMC Metolose 60SH-50 | 6.66 | 6.66 | 6.66 |
| HPMC Pharmacoat 603 | 6.66 | 6.66 | 6.66 |
| Glycerol | 1.08 | 1.08 | 1.08 |
| Ethanol:water solvent | 78.50 | 78.50 | 78.50 |
| Ethanol wt % in that solvent | 45 | 40 | 35 |

No particles were observed in any of WM4, WM5 or WM6 after preparation or after 3 days. Upon evaporation in oven at 50° C., particles were however observed in all three vessels.

Conclusions

For the pH approach, it was concluded:
that the solution obtained in step 1 of the preparation procedure described in Example 1 preferably should be adjusted to pH2.4 or lower to avoid the occurrence of midazolam-related precipitation, and
that the addition of midazolam HCl alone—albeit having a pH lowering effect—is not sufficient to create or maintain such pH, i.e. active pH-lowering with HCl or other pH-lowering agent is needed.
For the ethanol approach, it was concluded:
that using ethanol as co-solvent in the wet mix obtained in step 2 of the preparation procedure described in Example 1 will avoid the occurrence of midazolam-related precipitation,
that this can be achieved with an ethanol:water solvent with as little as 35 wt % ethanol, but
that at least 45 wt % ethanol is preferable.
It was decided to use these insights to prepare films based on HPMC and PVA, respectively.

Example 5. PVA Solubility in Ethanol Solution

The aim was to evaluate the ethanol approach for films made with PVA.

Methods

PVA Gohsenol EG-05PW, PVA Gohsenol EG-40PW, water and ethanol were used. Solubility study was made in a volume of 50 mL, with manual stirring. The total amount of polymer that was added corresponded to 13 wt % of the solution. Visual observation was used to assess the results.

Results

It was found that a 1.0:1.2 mix of PVA Gohsenol EG-05PW and PVA Gohsenol EG-40PW, when added as a total of 13 wt % to a solvent consisting of 80 wt % ethanol in water and with 4.5 wt % glycerol, did not dissolve. Other ratios between PVA Gohsenol EG-05PW and PVA Gohsenol EG-40PW were also tested (within 1.0:1.5 and 1.5:1.0), with similar results.

Conclusions

It was concluded that the ethanol approach for achieving a stable wet mix with dissolved midazolam HCl is not feasible when using a mix of PVA Gohsenol EG-05PW and PVA Gohsenol EG-40PW as film-forming polymer.

Example 6. HPMC and PVA Films with High Drug Load

Based on the findings in Examples 3, 4 and 5, it was decided to prepare films based on the abovementioned pH approach in combination with both HPMC and PVA, but to prepare films based on the abovementioned ethanol approach only in combination with HPMC.

Methods

The formulations studied, A5, A6 and A7, had rather similar compositions as A3 and A4, respectively, except that microcrystalline cellulose was not used. The preparation procedure as described in Example 1 was used but with the following exceptions:
For A5, A6 and A7: portions of the solutions obtained in step 1 and step 2, respectively, were set aside for being separately studied later.
For A5: in step 1 of the preparation, the solvent was an ethanol:water solution with 80 wt % ethanol.
For A6 and A7: in step 1 of the preparation, the solvent (water) was first acidified with 1M HCl to achieve pH1.47.
When assessing the results, focus was on general visual appearance, mechanical properties and microscopic studies of the solution set aside from step 1 and step 2. Normal light microscopy as well as cross-polarized light microscopy were used.

Results

The figures in rows 1-6 refer to the concentration of each component (wt %) in the resulting dry film, and rows 7-9 refer to the wet mix.

| Formulation: | | | |
|---|---|---|---|
| | A5 (Ethanol approach) | A6 (pH approach) | A7 (pH approach) |
| Midazolam HCl | 33.3 | 32.3 | 32.3 |
| HPMC Metolose 60SH-50 | 28.7 | 29.9 | |
| HPMC Pharmacoat 603 | 24.0 | 24.7 | |
| PVA Gohsenol EG-05PW | | | 29.9 |
| PVA Gohsenol EG-40PW | | | 24.7 |
| Glycerol | 14.0 | 13.1 | 13.1 |
| Wet mix batch size | 25 g | 14.5 g | 14.5 g |
| Dry content of wet mix (wt %) | 30.0 | 25.1 | 25.1 |
| Midazolam HCl in wet mix (wt %) | 10.0 | 8.1 | 8.1 |

It was found that all wet mixes (step 2) could be made satisfactory according to the preparation procedure. No undissolved particles were observed in the solutions set aside from step 1 and step 2. However, the A7 film developed a sticky character and adhered to the glass plate used in step 3 of the preparation procedure, leading to difficulties removing it in one piece in step 5. Furthermore, upon storage for even less than one week, A7 developed a characteristic "chemical" odour. The odours and the very sticky character of A7 were considered to indicate some kind of chemical degradation of the film forming polymer, assumably caused by the very low pH.

Conclusions

It was concluded:
that using the pH approach, as a way to achieve a stable wet mix with high levels of dissolved midazolam HCl, is not compatible with using PVA as the film forming polymer, and
that when using HPMC as the film forming polymer, both the pH approach and the ethanol approach are feasible.
It was decided to focus on using the ethanol approach, in combination with HPMC as film-forming polymer, for the next steps in the development of an optimal formulation.

Example 7. Large Scale Batch Based on HPMC and the Ethanol Approach

Based on the findings in previous examples, it was decided to prepare a batch with batch size and equipment typically used for manufacturing oral film batches for the market.

Methods

The formulation studied, A8, had a rather similar composition as A5. The preparation procedure was similar to that described in Example 1 with the exception of size and equipment and that it was a continuous process. Said large scale process is here described:
1. The ingredients, except the film forming polymer(s), were dissolved in an ethanol:water solvent with 44 wt % ethanol, during mixing, until a homogeneous solution was obtained with no solid content. The tank used was equipped with a rotor stator mixer and a scraper blade, and had a volume of 15 L. The order of adding was water, ethanol, glycerol, midazolam HCl and yellow iron oxide, and the mixing speeds varied between 500 rpm to 1300 rpm.
2. The film forming polymers were added, first Pharmacoat and then Metolose, during mixing, ending with a final thorough mixing using rotor stator speed of 2000 rpm and 20 rpm for the scraper during 52 minutes. The resulting wet mix was left to degass and removing bubbles overnight.
3. Using a continuous coating and drying system, a film batch was manufactured using a unique set of process parameters with regard to tunnel temperature profiles, blade opening and coating speed which determines the time spent in drying tunnel. Said continuous coating and drying system had a length of 12 m. It had four drying areas with individual temperature control system with film unwinding station before tunnel and winding station after tunnel and with a coating station made of a metal cylinder and a blade, which allow to drop a precise quantity of wet mix on the liner.
4. The resulting final, dry, film batch was stored on a mother roll, which was subsequently converted with a slitting and converting equipment in which mother rolls can be split into daughter rolls and the film on a daughter rolls can be slit into the desired film piece size (e.g. 1.5×2.5 cm) in which case the process liner can also be removed.
5. After the batch was converted to film pieces, a sufficient number of these film pieces were then packaged into pouches (primary packaging material) using a packaging machine.
6. During step 4 and after step 5, film units were assessed with regard to visual appearance, dry film coating weight (g/m$^2$), loss on drying, residual ethanol (internal gas chromatography method), assay (midazolam content, by HPLC), in vitro dissolution (test apparatus 2 USP and Eur. Ph. 2.9.3 paddles, and UV analysis) and other tests.

Results

The figures in rows 1-5 refer to the concentration of each component (wt %) in the resulting dry film, and rows 6-8 refer to the wet mix.

| Formulation: | A8 |
|---|---|
| Midazolam HCl | 33.0 |
| HPMC Metolose 60SH-50 | 24.2 |
| HPMC Pharmacoat 603 | 28.8 |
| Glycerol | 13.5 |
| Yellow iron oxide (E172) | 0.5 |
| Wet mix batch size | 5 kg |
| Dry content of wet mix | 21.5 wt % |
| Midazolam HCl in wet mix | 7.1 wt % |

One wet mix batch was prepared according to materials and methods above, but the conditions and parameters in step 3 were varied which resulted in eight sub-batches, each one with a unique set of process parameters with regard to tunnel temperature profiles (4 zones, lowest temp 60° C. and highest 110° C.), blade opening (580-620 μm) and coating speed which determines the time spent in drying tunnel (20-40 minutes).

It was found that the most optimal conditions were represented by a sub-batch (here identified as "Trial 7") that had drying temperatures between 80° C. and 110° C., blade opening of 580 µm and time spent in drying tunnel 40 minutes. The dry film thickness of that sub-batch was manifested as a dry coat weight of 84.6 g/m², and the test for loss-on-drying showed 4.1% and the residual ethanol test showed 3463 ppm. The average weight of one 1.5×2.5 cm film piece was 34.8 mg and the Assay showed an average content of 101.2% of the target value which was 10 mg midazolam (base) per film unit. The in vitro dissolution rate was high, with 101.4% released at 10 minutes.

In other sub-batches, during step 4, the test for loss-on-drying showed between 7.0-12.9% and residual ethanol values between 8 993-31 725 ppm, but these sub-batches were not progressed to step 5.

Conclusions

It was concluded:

that the formulation in this Example 7 is potentially feasible, the manufacturing procedure, including the ethanol approach, is feasible, and that process parameters, especially drying conditions, have a large influence over the resulting film quality.

It was decided to continue using this manufacturing procedure including the ethanol approach, and to continue using this formulation concept i.e. HPMC as film-forming polymer, glycerol as plasticizer and a drug load of 33 wt % (as the HCl salt).

Example 8. Short-Term Stability Study

The aim of this example was to study the short-term stability and how it depends on the packaging conditions.

Methods

A sub-batch, here identified as "Trial 10", was prepared with the same composition and process as the sub-batch Trial 7 in Example 8 with the exception of blade opening which was 620 µm instead of 580 µm. Film units obtained during step 5 were split into two groups:

Group C-1, which were packaged into sealed pouches intended for made of high barrier laminate manufactured by Danapak Flexibles A/S (Denmark), the same day as manufacturing (day zero).

Group C-3, which was placed in a conventional plastic pouches (day zero), and thus not protected from air humidity or oxygen.

At certain timepoints, the film units were taken out of the packages and observed visually with the naked eye as well as with non-polarized light microscopy. The observed film pieces were discarded i.e. not subjected to further observations.

Results

When observed at day 5, C-1 films showed the desired yellow, smooth appearance with no occurrence of particles or other irregularities except for some bubbles which had been formed during manufacturing. The microscopy did not show any particles or irregularities either.

C-3 films, on the other hand, showed whitish irregularities, which was also confirmed by microscopy observations of particles. It was further believed that the difference between C-1 and C-3 was mainly due to the larger air humidity exposure for the latter.

When observed at day 12, C-1 films showed similar whitish irregularities as did C-3 films at day 5, and similar observations were made by microscopy. For the C-3 films, said structures had continued to develop.

Conclusions

It was concluded that midazolam related particles may be formed upon storage.

It was decided to try to further optimize the formulation to reduce this phenomenon.

Example 9. Optimization of Plasticizer Level

It was hypothesized that the type and concentration of plasticizer could have an impact on the formation of midazolam-related particles in the dry film, and that the lower the concentration, the less formation of particles. The aim with this example was to test different levels of glycerol as plasticizer.

Methods

The formulation studied, A9, A10 and A11, had a similar composition as A8 except that the glycerol levels varied. The preparation procedure was similar to that described in Example 1 except for the size and equipment: Mixing equipment was a 4 blade shank, 400 mm diameter with motor from Janke&Kunkel (IKA labortechnik, RW20DZM), the coating equipment was a manual coating table type K control coater (RK Print Coat Instruments Ltd, UK), and the wet mix batch size was 200 g. Assessment methods were visual observation and microscopy.

Results

The figures in rows 1-5 refer to the concentration of each component (wt %) in the resulting dry film, and rows 6-8 refer to the wet mix.

| | Formulation: | | |
|---|---|---|---|
| | A9 | A10 | A11 |
| Midazolam HCl | 33.0 | 33.0 | 33.0 |
| HPMC Metolose 60SH-50 | 26.5 | 31.0 | 33.5 |
| HPMC Pharmacoat 603 | 26.5 | 31.0 | 33.5 |
| Glycerol | 14.0 | 5.0 | 0.0 |
| Yellow iron oxide (E172) | 0.0 | 0.0 | 0.0 |
| Wet mix batch size | 200 g | 200 g | 200 g |
| Dry content of wet mix | 21.5 wt % | 21.5 wt % | 21.5 wt % |
| Midazolam HCl in wet mix | 7.1 wt % | 7.1 wt % | 7.1 wt % |

The mechanical properties were assessed with the method described in Example 1. It was found that both A9 and A10 had good mechanical properties, ranked as 1 according to Example 1. Formulation A11, on the other hand, ranked as 2 and especially it did not break well along a straight line. It was also cut with razor blad after which the cutted edge had an uneven, cracky character, which was not the case for A9 and A10.

After one week of storage at 25° C. in a conventional plastic pouch (i.e. not protected against air and humidity exposure), A9, but not A10 or A11, had developed the whitish character described in Example 8, which can be seen in FIG. 1. Similar observations were made after two weeks.

From these results it can be seen that 5% glycerol is preferred compared with 0% and 14% because 5% combines acceptable mechanical properties (i.e. plasticizing effect) with an acceptable stability.

Conclusions

It was concluded that formulation A10 (5% glycerol) is superior to formulations A9 (14%) and A11 (0%), as well as to the formulation A8 (13.5%) that was made in large industrial scale in Example 7.

It was decided to use this new formulation A10, for the next large scale batch.

Example 10. Large Scale Batch Based on HPMC and the Ethanol Approach and 5% Plasticizer Example 7 had confirmed the feasibility of the manufacturing process and Example 9 had identified a new and better composition. These two findings were now combined.

Methods

Methods as in Examples 7 (Trial 7) and Example 9 were used. The formulation studied, A12, had a similar composition as A10 in Example 9, with the exception that 1% pigment was added. The preparation procedure was similar to that described in Example 7, with the exception that blade opening for wet film coating as 620 µm and that only one film batch was made from the wet mix batch (i.e. not several sub-batches). The same assessment methods as in Example 7 and 9 were used. A stability study was also started.

The dissolution rate was measured for formulation A12 using the United States Pharmacopeia (USP) Dissolution Apparatus 2—Paddle (37° C.±0.5° C.). The dissolution testing was performed at 75 rpm in 1000 mL phosphate buffer pH 6.8. The content of midazolam was determined by using UV spectroscopy (240 nm).

Results

The figures in rows 1-5 refer to the concentration of each component (wt %) in the resulting dry film, and rows 6-9 refer to the wet mix.

| Formulation: | A12 |
| --- | --- |
| Midazolam HCl | 33.0 |
| HPMC Metolose 60SH-50 | 30.5 |
| HPMC Pharmacoat 603 | 30.5 |
| Glycerol | 5.0 |
| Yellow iron oxide (E172) | 1.0 |
| Ethanol in the ethanol:water solvent | 45 wt % |
| Wet mix batch size | 5 kg |
| Dry content of wet mix | 21.5 wt % |
| Midazolam HCl in wet mix | 7.1 wt % |

The solution obtained in step 1 (of the preparation procedure described in Example 7) before adding the pigment was checked for the absence of particles by visual observation and microscopy and so was the wet mix obtained in step 2. The final, stable pH of the solution as well as the wet mix was pH3.3.

The dry film thickness of the batch was manifested as a dry coating weight of 89.1 g/m$^2$ (target was 90.0 g/m$^2$), and the test for loss-on-drying showed 3.9% and the residual ethanol test showed 14 365 ppm. The Assay showed an average content of 99.8% of the target value which was 10 mg midazolam (base) per film unit. In vitro disintegration time was 25 seconds. The dissolution results were:

| Time | Amount dissolved (%) | | |
| --- | --- | --- | --- |
| | Minimum | Maximum | Mean |
| 5 min | 82.6 | 90.6 | 87 |
| 10 min | 91.5 | 95.8 | 94 |
| 15 min | 94.4 | 97.1 | 96 |
| 30 min | 95.8 | 98.1 | 97 |
| 45 min | 96.2 | 98.4 | 97 |
| 60 min | 96.3 | 98.6 | 97 |
| 120 min | 96.5 | 98.9 | 98 |
| 240 min | 96.8 | 99.3 | 98 |
| 360 min | 97.0 | 99.6 | 98 |

Those dissolution results were representative also for dissolution tests at different timepoints and storage conditions in the stability study below.

Stability Study:

After 12 months storage at 5° C. and ambient % RH, the Assay was 101.2%. However, the visual appearance was not fully compliant: there was a development of whitish spots such as those described in Example 8 and 9.

Conclusions

It was concluded that:

the composition and the preparation method described in this Example 10 are feasible, the resulting product was feasible for being studied in human clinical studies, but that the development of particles at higher storage temperatures needs to be further studied.

It was decided to continue to human clinical studies.

Example 11. Human Bioavailability Study

In Example 10 it was shown how a feasible product was achieved, based on the initial hypotheses and other targeted characteristics such as manufacturability and stability, as well as a relatively fast dissolution yet not having an instantaneous dissolution. The aim in this Example 11 was to study the bioavailability of this product in comparison with a buccal solution.

Methods

A batch (A13) with the same size, composition, materials and manufacturing process as batch A12 in Example 10 was made, but with the main difference that A13 was made under GMP conditions.

After being analysed similarly to Example 10 and subject to other quality related controls, the batch was approved and released for being used in human clinical trials. A comparative bioavailability study was then made at well-renowned clinical contract research organization (CRO) located in the European Union.

The study was a non-blinded, single dose, randomized, cross-over study. 24 healthy, adult, male volunteers were included in the study after being assessed with regard to a number of inclusion and exclusion criteria. These inclusion and exclusion criteria were related the general health status as well as aspects related specifically to the treatments (e.g. hypersensitivity to midazolam). The treatments were given when the study subjects were in fasting state i.e. had not eaten for several hours before the dosing. The study complied with ICH E6 (R2) Guideline for Good Clinical Practice. The Declaration of Helsinki, as last amended and accepted by the 64th World Medical Association General Assembly, Fortaleza, Brazil, October 2013, as well as other applicable guidelines, directives and regulations. Two treatments were T1: The buccal midazolam film, with 10 mg midazolam (base), applied on the buccal mucosa of the inside of one cheek.

R: Buccolam oromucosal solution, of the 10 mg midazolam (base) strength which has a volume of 2 mL, half of which was applied on the buccal mucosa of the inside of one cheek and the other half in the other cheek.

For each treatment, the subjects were instructed not to intentionally swallow the products or the saliva solution being accumulated, since swallowing will decrease the overall bioavailability because the oral-gastrointestinal bioavailability of midazolam is lower than the buccal-transmucosal bioavailability. Further, the oral-gastrointestinal bioavailability typically suffers from higher intra- and interindividual variability than the buccal-transmucosal bioavailability. However, the subjects were instructed to empty their mouth of excess saliva at 5 minutes and at 10 minutes after the products had been administered. This was partly for ethical and study compliance reasons (because, saliva has to go somewhere), and partly to mimic drooling, which often occurs in patients with seizures.

After being given the treatment, blood samples were withdrawn at 0.16, 0.33, 0.50, 0.67, 0.83, 1.00, 1.25, 1.50, 1.75, 2.00, 2.50, 3.00, 4.00, 6.00 and 8.00 hours post-dose. Including the pre-dose sample (within 1.00 h before dosing), the total number of blood collections in each study period was thus 16.

A HPLC/MS/MS method was used for the bioanalysis of these samples. The samples were first isolated from plasma by protein precipitation. The analytical methods then used 50 μL of plasma sample for each analysis. The method was validated for concentrations as low as 0.20 ng/mL of midazolam in plasma. A weighted linear regression was evaluated over the concentration range 0.20-200.00 ng/mL of midazolam in plasma. The equipment used for HPLC/MS/MS method (here identified as HPLC/MS/MS TSQ-08) was:

HPLC system: pumps ACCELA 1250 and ACCELA 600 (Flux Instruments), autosampler PAL HTS-xt (CTC Analytics) and ten-port switching valve SelectPro (Alltech)

MS detector: TSQ Vantage (ThermoFisher Scientific)

Guard column: Luna C18(2) Mercury, 20×4.0 mm, 5 μm, Phenomenex

Column: Kinetex PhenylHexyl, 100×3 mm, 5 μm, Phenomenex

Injection: 10 μL

Acquisition: mode: HESI; scan: MS/MS (SRM)

Mobile phase: ACN, MeOH, 160 mM HCOONH4, water

In addition to the experimental samples corresponding to the abovementioned timepoints, each subject also provided samples for suitability test, plasma blank, zero sample, calibration samples, and quality control samples.

Phoenix WinNonlin software was used for the pharmacokinetic parameters calculation based on the bioanakytical results. A non-compartmental model for evaluation in plasma after single-dose extravascular dosing using Linear Trapezoidal/Linear Interpolation calculation method was used. The best-fit method with uniform weighting and without any exclusion was used for the terminal elimination rate constant calculation in all cases. The drug concentration in plasma at each sampling time point was presented for each product for each subject. The descriptive statistics: arithmetic mean, standard deviation, coefficient of variation, maximal value, minimal value, median value, and geometric mean were also presented. Data were summarized as the concentration versus time profiles for-each product in graphs for each Subject as well as for mean values. A formal statistical assessment of so-called bioequivalence was not made.

Results

Analysis of the Batch:

The analytical results were: Assay 97.4%, Total related substances 0.16%, Dissolution after 10 minutes 96%, loss-on-drying was 3%, residual ethanol was <30 000 ppm, Total aerobic microbial count (TAMC) was <1 cfu/g, Total combined yeasts and moulds count (TYMC) was <1 cfu/g, total absence of *Staphylococcus aureus* and *Pseudomonas aeruginosa*, and the visual appearance was compliant.

Results of the Comparative Bioavailability Study:

All the included 24 subjects carried through the whole study and were subject to the eventual statistical evaluation. The results are presented in FIG. 2 as the graph of mean values. The geometric least squares mean for Cmax (ng/mL) and AUC0-t were:

| | Treatment: | |
| | T1 (film, unilateral) | R (Buccolam bilateral) |
| --- | --- | --- |
| Cmax (ng/mL) | 64.32 | 35.58 |
| AUC0-t (ng*h/mL) | 223.65 | 102.71 |

Conclusions

It was concluded that the bioavailability of the buccal film had a significantly higher bioavailability than the buccal solution.

Example 12. Testing Triethyl Citrate (TEC) as Plasticizer

Despite the successful pharmaceutical and clinical studies presented in Examples 10 and 11, there was an aim to study potential improvements in the long term physical stability. In Example 9 it was shown that the concentration of plasticizer had an impact on the long term stability, and therefore it was hypothesised that also the type of plasticizer could matter. TEC has been proposed in the literature as an effective plasticizer for oral films.

Methods

A preparation method as in Example 9 was used. The formulations studied, A14-A16, had a similar composition as in Examples 10 and 11, except that the type and level of plasticizer were different. Assessment methods were mechanical properties, visual observation and microscopy, as previously described. Focus was on the occurrence of particles and their potential growth over time. There were thus no attempts to make pharmaceutical analyses such as assay or in vitro dissolution, and no attempts to make any in vivo studies because it was not believed that the precise type and level of plasticizer would have any major impact on those properties.

Results

The figures in rows 1-5 refer to the concentration of each component (wt %) in the resulting dry film, and rows 6-9 refer to the wet mix.

|  | Formulation: | | |
| --- | --- | --- | --- |
|  | A14 | A15 | A16 |
| Midazolam HCl | 33.0 | 33.0 | 33.0 |
| HPMC Metolose 60SH-50 | 28.5 | 31.0 | 31.5 |
| HPMC Pharmacoat 603 | 28.5 | 31.0 | 31.5 |
| Triethyl citrate (TEC) | 10.0 | 5.0 | 3.0 |
| Yellow iron oxide (E172) | 0.0 | 0.0 | 1.0 |
| Wet mix batch size | 60 g | 60 g | 200 g |
| Ethanol in the ethanol:water solvent | 50 wt % | 50 wt % | 45 wt % |
| Dry content of wet mix | 21.5 wt % | 21.5 wt % | 21.5 wt % |
| Midazolam HCl in wet mix | 7.1 wt % | 7.1 wt % | 7.1 wt % |

It was first found that both A14 and A15 had good mechanical properties, ranked as 1 according to the principles laid out in Example 1. There were some minor observations that Formulation A15 had cracky edges upon cutting, but A15 was nevertheless deemed satisfactory with regard to the mechanical properties.

Next, the short term stability of A14 and A15, as measured with visual observation and microscopy, was studied after storage at 5° C., 25° C. and 40° C. for up to 16 weeks. At 25° C. there was a significant difference between A14 (10% TEC) and A15 (5%), with A14 showing whitish appearance and particles observed by microscopy, i.e. clear indications of inferior stability.

As A15 (5% TEC) thus appeared viable both with regard to mechanical properties and physical stability, it was realized that an even lower level of TEC could prove to be even better.

Therefore, formulation A16 with 3% TEC was prepared. The resulting film was however quite brittle, and during the folding test described in Example 1, several samples broke after just one bending. It was therefore concluded that 3% TEC was not a sufficient level for achieving acceptable mechanical properties.

Conclusions

It was concluded that using 10% TEC as plasticizer is too high and using 3% is too low, if the aim is to achieve a viable product with comparable characteristics as the films used in Example 10 and 11.

Example 13. Testing Other Potential Plasticizers

Examples 9 and 12 demonstrated that the type and level of plasticizer are critical attributes of a midazolam film, and that above a certain level of plasticizer there is a risk for the development of midazolam-related particles. The aim of this example was to study other potential plasticizers.

Methods

Preparation methods as in Example 12 was used. Assessment methods were, as applicable, as in Example 12:

mechanical properties, visual observation and microscopy, as previously described. As in Example 12, focus was on the occurrence of particles over time.

Results

The figures in rows 1-6 refer to the concentration of each component (wt %) in the resulting dry film, and rows 7-10 refer to the wet mix.

|  | Formulation: | | |
| --- | --- | --- | --- |
|  | A17 | A18 | A19 |
| Midazolam HCl | 33.0 | 33.0 | 33.0 |
| HPMC Metolose 60SH-50 | 28.5 | 31.0 | 31.0 |
| HPMC Pharmacoat 603 | 28.5 | 31.0 | 31.0 |
| Sorbitol | 10.0 |  |  |
| Poloxamer 407 |  | 5.0 |  |
| Kollicoat IR |  |  | 5.0 |
| Wet mix batch size | 60 g | 200 g | 200 g |
| Ethanol in the ethanol:water solvent | 50 wt % | 45 wt % | 45 wt % |
| Dry content of wet mix | 21.5 wt % | 21.5 wt % | 21.5 wt % |
| Midazolam HCl in wet mix | 7.1 wt % | 7.1 wt % | 7.1 wt % |

It was found that A17 (sorbitol, 10%) resulted in very brittle films, which were so poor that they were not even subjected to further mechanical testing. A formulation A17b with 5% sorbitol was also made, but showed similar poor mechanical properties.

It was found that A18 (poloxamer 407, 5%) resulted in films with very good mechanical properties, which, when subjected to mechanical testing according to Example 1, could be folded more than 10 times without breaking and which broke in a straight line when pulled apart. However, upon 4 weeks storage at 25° C., the films became whitish and particles were observed inside the film when using microscopy.

It was found that A19 (Kollicoat IR, 5%) resulted in films with similar good mechanical properties as A18. Already after the preparation, the visual appearance was somewhat whitish but in a homogenous way that was not believed to indicate midazolam-related particles, and no such particles could be seen with microscopy. Upon 4 weeks storage at 25° C., the films still had that satisfactory visual appearance and particles or structures were still not observed in microscopy. However, after 24 weeks, particles inside the films were observed when using microscopy, and these particles—contrary to the initial whitish appearance of the films—were believed to be midazolam-related.

The mechanical properties remained good.

Conclusions

It was concluded:

that sorbitol is not an effective plasticizer in a film containing high level of midazolam and using HPMC as film-forming polymer, that poloxamer 407 and Kollicoat IR are effective plasticizers at levels as low as 5%, in a film containing high level of midazolam and using HPMC as film-forming polymer, and that Kollicoat IR (5%) results in a somewhat better stability than poloxamer 407 (5%) but yet not fully satisfactory.

Example 14. Kollicoat IR as Film Polymer

Kollicoat IR has also been proposed as a film-forming polymer for oral films, which is something different from being used as a plasticizer additive alongside another film-forming polymer such as for example HPMC.

Methods

Preparation method as in Example 12 was used, except for ethanol level and dry content as explained below.

Results

The figures in rows 1-2 refer to the concentration of each component (wt %) in the resulting dry film, and rows 3-6 refer to the wet mix.

| Formulation: | A20 |
| --- | --- |
| Midazolam HCl | 33.0 |
| Kollicoat IR | 67.0 |
| Wet mix batch size | 200 g |
| Ethanol in the ethanol:water solvent | 34 wt % |
| Dry content of wet mix | 27.3 wt % |
| Midazolam HCl in wet mix | 9.0 wt % |

Compared with previous Examples, e.g. Examples 10, 12 and 13, the ethanol level was lower and the dry content of wet mix was higher. The reason for this was to render the wet mix a viscosity that was feasible for coating into a wet film. These levels had been determined in placebo experiments preceding this example but not being presented here.

It was found that A20 resulted in a film with very good mechanical properties, which were similar to those reported for A18 and A19 in Example 13. However, already soon after the preparation, i.e. without even a short term storage test, there were whitish spots in the film that were interpreted as midazolam-related particles.

Conclusions

It was concluded that Kollicoat IR as the sole film-forming polymer is not feasible.

REFERENCES

Jithendra et al., Panacea Journal of Pharmacy and Pharmaceutical Sciences (2015), 4:4, 801-816
Soroushnai et al., Current Drug Delivery (2018), 15, 9, 1294-1304
Wasilevska, K. et al., Acta Pharm. (2019), 69, 155-176
WO 2017/009446 [Sjögren, C.]
Rogawski et al., Epilepsy & Behavior (2019), Volume 101, Part B, 106537
CN 1 830 447 A
Kathpalia et al., Current Drug Delivery (2013), 10, 667-684

The invention claimed is:

1. A unit dosage form in a form of an oral film comprising:
   a) at least 20 wt % (defined as a base) midazolam or a pharmaceutically acceptable salt thereof; and
   b) 35 to 70 wt % HPMC (hydroxypropyl methylcellulose), wherein the HPMC is a mixture of:
   Hypromellose 2910, 3 mPa·s; and
   Hypromellose 2910, 50 mPa·s
with the proviso that a sum of the wt % of the components does not exceed 100 wt %.

2. The unit dosage form according to claim 1, wherein a concentration of midazolam, or a pharmaceutically acceptable salt thereof, is 25 to 40 wt % (defined as the base).

3. The unit dosage form according claim 1, wherein the unit dosage form comprises 2.5 to 20 mg (defined as the base) of midazolam or a pharmaceutically acceptable salt thereof.

4. The unit dosage form according to claim 1, wherein the unit dosage form comprises 50 to 65 wt % HPMC.

5. The unit dosage form according to claim 1, wherein a ratio of Hypromellose 2910, 3 mPa·s and Hypromellose 2910, 50 mPa·s is 4:1 to 1:4.

6. The unit dosage form according to claim 1, wherein the unit dosage form comprises:
   a) at least 20 wt % midazolam or a pharmaceutically acceptable salt thereof;
   b) 35 to 70 wt % HPMC, wherein the HPMC is a mixture of:
   Hypromellose 2910, 3 mPa·s; and
   Hypromellose 2910, 50 mPa·s; and
   c) 3 to 8 wt % plasticizer.

7. The unit dosage form according to claim 6, wherein the plasticizer is: glycerol; glycerol monoacetate; citric acid and esters thereof; diethylene glycol; ethylene glycol; fatty acid esters; PEG; polyethylene-propylene glycols; polypropylene glycol-polyethylene glycol copolymer; polyvinyl alcohol-polyethylene glycol copolymer; propylene glycol; phthalic acid; polyalkylene oxides; sorbitol; triacetin; or xylitol.

8. The unit dosage form according to claim 6, wherein the midazolam or pharmaceutically acceptable salt thereof is midazolam hydrochloride.

9. The unit dosage form according to claim 6, further comprising 0.5 to 5 wt % of one or more colorants, and/or one or more flavouring agents.

10. The unit dosage form according to claim 6, wherein at least 85% of the midazolam, or pharmaceutically acceptable salt thereof, has been dissolved within 10 minutes but no more than 95% has been dissolved within 5 minutes in a USP Dissolution Apparatus 2—Paddle.

11. The unit dosage form according to claim 1, wherein the unit dosage form comprises:
    a) 20 to 25 wt % midazolam hydrochloride;
    b) 65 to 70 wt % wherein the HPMC is a 1:4 mixture of Hypromellose 2910, 3 mPa·s, and Hypromellose 2910, 50 mPa·s;
    c) 5 wt % of one or more colorants, and/or one or more flavouring agents; and
    d) 3 wt % PEG,
with the proviso that the sum of the wt % of the components does not exceed 100 wt %.

12. A process for producing a unit dosage according to claim 1, the process comprising the steps of:
    a) mixing the midazolam or a pharmaceutically acceptable salt thereof and the HPMC in a solvent to provide a wet mix; and
    b) casting the wet mix obtained in step a) and drying it to provide a final film.

13. The process according to claim 12, wherein the process comprises the steps of:
    a) mixing the midazolam, or a pharmaceutically acceptable salt thereof, and the HPMC in a solvent to provide a homogenous wet mix in which midazolam, or the pharmaceutically acceptable salt thereof, is dissolved; and
    b) casting the wet mix obtained in step a), drying it to provide a final, dry film in which the midazolam, or pharmaceutically acceptable salt thereof, is still dissolved.

14. The process according to claim 12, wherein step a) comprises the steps of:

i)
  1) dissolving the midazolam, or a pharmaceutically acceptable salt thereof, in process solvent to obtain a homogenous solution;
  2) optionally adding a plasticizer and/or a pigment to the solution in a) and mixing to obtain a homogenous solution; and
  3) adding the HPMC to the solution and mixing to obtain the wet mix;
  or
ii)
  1) mixing the HPMC in process solvent to obtain a homogenous solution; and
  2) adding the midazolam, or a pharmaceutically acceptable salt thereof, and optionally a plasticizer and/or a pigment to the solution in a) and mixing to obtain the wet mix;
and/or step b) comprises the steps of:
  1) coating the wet mix onto an inert intermediate layer, thus forming a wet film;
  2) drying the wet film; and
  3) removing the intermediate layer to provide the final film.

15. The process according to claim 12, wherein the solvent is a mixture of water and ethanol and a ratio of water and ethanol is 60:40 to 40:60, and a pH adjustment is made to achieve pH 1.5 to 2.4 in the wet mix or in any of the liquid states preceding final preparation of the wet mix.

16. The process according to claim 12, wherein the wet film is dried until a residual ethanol content is no more than 5 wt %.

17. A method for acute treatment of seizures comprising administering a unit dosage form according to claim 1 to a subject in need thereof.

18. The method according to claim 17, wherein the seizures are caused by epilepsy, fever caused by malaria, fever of other causes, poisoning, tetanus, brain tumours, Lennox-Gastaut syndrome, tuberous sclerosis complex and/or Dravet syndrome.

19. The method according to claim 17, wherein the film provides a plasma drug concentration-time profile of midazolam, or a pharmaceutically acceptable salt thereof, where a mean $C_{max}$ is 80% to 125% of 64.32 ng/ml (CV 7.05%) after administration with a single unit dosage form comprising 10 mg midazolam (defined as base) applied on a buccal mucosa.

20. The method according to claim 17, wherein the film provides a plasma drug concentration-time profile of midazolam, or a pharmaceutically acceptable salt thereof, where a mean $AUC_{0-t}$ is 80% to 125% of 223.65 ng*h/mL (CV 5.33%) after administration with a single unit dosage form comprising 10 mg midazolam (defined as base) applied on a buccal mucosa.

* * * * *